US012749197B2

(12) United States Patent
Healey et al.

(10) Patent No.: US 12,749,197 B2
(45) Date of Patent: *Sep. 29, 2026

(54) METHOD AND SYSTEM FOR CALCULATING A POINT ESTIMATE OF AN ULTRASOUND DOSE

(71) Applicant: EXACT THERAPEUTICS AS, Oslo (NO)

(72) Inventors: Andrew John Healey, Moss (NO); Svein Kvåle, Ås (NO); Ola Myhre, Haslum (NO)

(73) Assignee: Exact Therapeutics AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 19/127,392

(22) PCT Filed: Nov. 3, 2023

(86) PCT No.: PCT/NO2023/060084

§ 371 (c)(1),
(2) Date: May 5, 2025

(87) PCT Pub. No.: WO2024/096748

PCT Pub. Date: May 10, 2024

(65) Prior Publication Data

US 2026/0007393 A1 Jan. 8, 2026

(30) Foreign Application Priority Data

Nov. 4, 2022 (NO) .................................... 20221187

(51) Int. Cl.
*G06T 7/11* (2017.01)
*A61B 8/00* (2006.01)
(Continued)

(52) U.S. Cl.
CPC .................. *G06T 7/11* (2017.01); *A61B 8/06* (2013.01); *A61B 8/4245* (2013.01); *A61B 8/469* (2013.01);
(Continued)

(58) Field of Classification Search
CPC ....... A61B 8/5207; A61B 8/06; A61B 8/4245; A61B 8/469; A61B 8/481; G06T 7/11
See application file for complete search history.

(56) References Cited

U.S. PATENT DOCUMENTS 6,165,440 A 12/2000 Esenaliev
8,345,821 B2 1/2013 Sumanaweera et al.
(Continued)

FOREIGN PATENT DOCUMENTS

CN 108815725 A 11/2018
EP 0727225 A3 1/1997
(Continued)

OTHER PUBLICATIONS

Andersen et al., "A harmonic dual-frequency transducer for acoustic cluster therapy." Ultrasound Med Biol. Sep. 1, 2019;45(9):2381-2390.

(Continued)

*Primary Examiner* — Peter Luong
(74) *Attorney, Agent, or Firm* — Knobbe, Martens, Olson & Bear LLP

(57) ABSTRACT

A method for creating a medium property map of a region of interest of a subject, wherein the medium property map provides a plurality of different medium property values in different segments of the region of interest dependent on the medium within each of said segments, comprising: obtaining an image of the region of interest, wherein the region of interest comprises a target treatment area and a surrounding region of the target treatment area; processing the image to
(Continued)

identify different components of the region of interest; segmenting and categorizing the different components into predetermined media categories; retrieving a medium property value associated with each media category and attributing said medium property value to each respective component of the segmented region of interest.

20 Claims, 11 Drawing Sheets

(51) Int. Cl.
*A61B 8/06* (2006.01)
*G06T 7/00* (2017.01)

(52) U.S. Cl.
CPC ............ *A61B 8/481* (2013.01); *A61B 8/5207* (2013.01); *G06T 7/0012* (2013.01); *G06T 2207/10081* (2013.01); *G06T 2207/10088* (2013.01); *G06T 2207/10132* (2013.01); *G06T 2207/30008* (2013.01); *G06T 2207/30024* (2013.01); *G06T 2207/30104* (2013.01)

(56) References Cited

U.S. PATENT DOCUMENTS

| | | | |
|---|---|---|---|
| 9,629,610 | B2 | 4/2017 | Sandstrom et al. |
| 10,544,224 | B2 | 1/2020 | Manekas et al. |
| 12,343,396 | B2 | 7/2025 | Healey et al. |
| 12,377,146 | B2 | 8/2025 | Healey et al. |
| 12,478,676 | B2 | 11/2025 | Healey et al. |
| 2003/0204141 | A1 | 10/2003 | Nock et al. |
| 2004/0081623 | A1 | 4/2004 | Eriksen et al. |
| 2006/0025756 | A1 | 2/2006 | Francischelli et al. |
| 2006/0078182 | A1* | 4/2006 | Zwirn .................. G06T 7/0012 382/128 |
| 2007/0178047 | A1 | 8/2007 | Kawabata |
| 2008/0242979 | A1 | 10/2008 | Fisher et al. |
| 2008/0299084 | A1 | 12/2008 | Brahmbhatt et al. |
| 2009/0252773 | A1 | 10/2009 | Yoneda et al. |
| 2010/0298709 | A1 | 11/2010 | Needles et al. |
| 2012/0165665 | A1 | 6/2012 | Sandstrom et al. |
| 2013/0046230 | A1 | 2/2013 | Lewis et al. |
| 2013/0131495 | A1 | 5/2013 | Konofagou et al. |
| 2013/0289398 | A1 | 10/2013 | Borden et al. |
| 2015/0258353 | A1 | 9/2015 | Partanen et al. |
| 2015/0273061 | A1 | 10/2015 | Trogler et al. |
| 2016/0243234 | A1 | 8/2016 | Healey et al. |
| 2017/0259086 | A1 | 9/2017 | Carpentier et al. |
| 2018/0200196 | A1 | 7/2018 | Fahmy et al. |
| 2018/0360420 | A1 | 12/2018 | Vortman et al. |
| 2019/0216478 | A1 | 7/2019 | Maxwell et al. |
| 2020/0254285 | A1 | 8/2020 | Jang et al. |
| 2020/0306564 | A1 | 10/2020 | Bar-Zion et al. |
| 2020/0323515 | A1 | 10/2020 | Levy |
| 2020/0405258 | A1 | 12/2020 | Dayton et al. |
| 2021/0106849 | A1 | 4/2021 | Liu et al. |
| 2021/0169515 | A1 | 6/2021 | Pahk et al. |
| 2021/0299256 | A1 | 9/2021 | Healey et al. |
| 2022/0002412 | A1 | 1/2022 | Xie et al. |
| 2022/0305139 | A1 | 9/2022 | Kim et al. |
| 2022/0378692 | A1 | 12/2022 | Sontum et al. |
| 2023/0211020 | A1 | 7/2023 | Kvale et al. |
| 2023/0218759 | A1 | 7/2023 | Healey et al. |
| 2023/0218760 | A1 | 7/2023 | Healey et al. |
| 2023/0233681 | A1 | 7/2023 | Healey et al. |
| 2023/0241216 | A1 | 8/2023 | Healey et al. |
| 2024/0216549 | A1 | 7/2024 | Sontum et al. |
| 2024/0269489 | A1 | 8/2024 | Kvåle et al. |
| 2024/0358984 | A1 | 10/2024 | Kvåle et al. |
| 2024/0359037 | A1 | 10/2024 | Sontum et al. |
| 2025/0235536 | A1 | 7/2025 | Kvåle et al. |

FOREIGN PATENT DOCUMENTS

| | | | |
|---|---|---|---|
| EP | 1842560 | | 10/2007 |
| EP | 2468191 | A1 | 6/2012 |
| EP | 2521593 | B1 | 11/2012 |
| EP | 3901172 | A1 | 10/2021 |
| EP | 4008358 | A1 | 6/2022 |
| EP | 4048231 | A1 | 8/2022 |
| GB | 2595513 | A | 12/2021 |
| JP | 2005168312 | | 6/2005 |
| JP | 2007197403 | | 8/2007 |
| JP | 2008526785 | | 7/2008 |
| JP | 2016-532718 | A | 10/2016 |
| JP | 2019-502657 | A | 1/2019 |
| WO | WO 1994/016379 | A1 | 7/1994 |
| WO | 96/39197 | A1 | 12/1996 |
| WO | WO 1998/001732 | A1 | 1/1998 |
| WO | WO 1998/017324 | | 4/1998 |
| WO | WO 1998/051284 | A1 | 11/1998 |
| WO | WO 1999/039738 | | 8/1999 |
| WO | 99/53693 | A1 | 10/1999 |
| WO | WO 1999/053963 | A1 | 10/1999 |
| WO | WO 1999/053965 | | 10/1999 |
| WO | WO 2005/063306 | | 7/2005 |
| WO | WO 2015/047103 | | 4/2015 |
| WO | WO 2017/080481 | | 5/2017 |
| WO | WO 2018/126322 | | 7/2018 |
| WO | WO 2019/094802 | | 5/2019 |
| WO | WO 2020/115491 | | 6/2020 |
| WO | WO 2021/045485 | | 3/2021 |
| WO | 2021/069971 | A1 | 4/2021 |
| WO | WO 2021/080438 | | 4/2021 |
| WO | WO 2021/118783 | | 6/2021 |
| WO | 2021/150446 | A1 | 7/2021 |
| WO | WO 2021/224921 | | 11/2021 |
| WO | 2021/239878 | A1 | 12/2021 |
| WO | WO 2022/069377 | | 4/2022 |

OTHER PUBLICATIONS

Aoki et al., "Image of tumor matastasis and inflammatory lymph node enlargement by contrast-enhanced ultrasonography," Word Journal of Radiology, Dec. 28, 2011, pp. 298-305.

Argenziano et al., Vancomycin-loaded nanobubbles: A new platform for controlled antibiotic delivery against methicillin-resistant *Staphylococcus aureus* infections. Int'l J Pharma. May 15, 2017;523(1):176-188.

Åslund et al., "Efficient Enhancement of Blood-Brain Barrier Permeability Using Acoustic Cluster Therapy (ACT)", Theranostics 2017, vol. 7, Issue 1, doi: 10.7150/thno. 16577.

Beccaria et al., "Ultrasound-induced opening of the blood-brain barrier to enhance temozolomide and irinotecan delivery: an experimental study in rabbits," Journal of Neurosurgery, vol. 124, No. 6, Jun. 1, 2016, pp. 1602-1610.

Brighi, "MR-guided focused ultrasound increases antibody delivery to nonenhancing high-grade glioma," Neuro-Oncology Advances, vol. 2, No. 1, Mar. 5, 2020 in 12 pages.

Bulner et al., "Enhancing Checkpoint Inhibitor Therapy with Ultrasound Stimulated Microbubbles," Ultrasound in Medicine and Biology, vol. 45, No. 2, Nov. 15, 2018, pp. 500-512.

Bush et al., "Acoustic Cluster Therapy displays theranostic capability in enhancing the effectiveness of liposomal doxorubicin treatment of human triple negative breast cancer in mice," In 2019 IEEE International Ultrasonics Symposium, Oct. 6, 2019, pp. 224-226.

Bush et al., "Ultrasound, optical and photoacoustic imaging of Acoustic Cluster Therapy enhanced delivery to human tumors in mice," In 2019 IEEE International Ultrasonics Symposium [IUS], Oct. 6, 2019, pp. 1556-1559.

Bush et al., "Therapeutic Dose Response of Acoustic Cluster Therapy in Combination With Irinotecan for the Treatment of Human Colon Cancer in Mice," Front Pharmacol. Nov. 19, 2019;10:1299 in 14 pages.

Bush et al., "Theranostic Attributes of Acoustic Cluster Therapy and Its Use for Enhancing the Effectiveness of Liposomal Doxorubicin

(56) References Cited

OTHER PUBLICATIONS

Treatment of Human Triple Negative Breast Cancer in Mice," Front Pharmacol. Feb. 20, 2020;11:75 in 11 pages.
Carpentier et al., "Clinical trial of blood-brain barrier disruption by pulsed ultrasound," Science Translational Medicine, vol. 8, No. 343, Jun. 15, 2016 in 8 pages.
Carter et al., "Immune-oncology agents for cancer therapy." Pharm. J. May 2020;304(7937): S2-S27.
Castle et al., "Ultrasound-mediated targeted drug delivery: recent success and remaining challenges". Am J Physiol Heart Circ Physiol. Feb. 2013;304(3):H350-7.
Chen et al., "Focused ultrasound-induced blood-brain barrier opening to enhance interleukin-12 delivery for brain tumor immunotherapy: a preclinical feasibility study," Journal of Translational Medicine, vol. 13, No. 1, Mar. 17, 2015 in 12 pages.
Chen et al., "Theranostic Strategy of Focused Ultrasound Induced Blood-Brain Barrier Opening for CNS Disease Treatment," Frontiers in Pharmacology, vol. 10, Feb. 7, 2019 in 14 pages.
Curley et al., "Focused Ultrasound Immunotherapy for Central Nervous System Pathologies: Challenges and Opportunities," Theranostics, vol. 7, No. 15, Jan. 1, 2017, pp. 3608-3623.
Dimcevski et al., "A human clinical trial using ultrasound and microbubbles to enhance gemcitabine treatment of inoperable pancreatic cancer", J Control Release, 2016, vol. 243, pp. 172-181, http://dx.doi.org/10.1016/j.jconrel.2016.10.007.
Goldwirt et al., "Enhanced brain distribution of carboplatin in a primate model after blood-brainbarrier disruption using an implantable ultrasound device," Cancer Chemotherapy and Pharmacology, Springer Verlag, vol. 77, No. 1, Dec. 8, 2015, pp. 211-216.
Healey et al. "Acoustic cluster therapy: in vitro and ex vivo measurement of activated bubble size distribution and temporal dynamics," Ultrasound in Med Biol. May 1, 2016;42(5): 1145-6611.
Jordao et al., "Antibodies Targeted to the Brain with Image-Guided Focused Ultrasound Reduces Amyloid-? Plaque Load in the TgCRND8 Mouse Model of Alzheimer's Disease," PLOS ONE, vol. 5, No. 5, May 1, 2010 in 8 pages.
Kinoshita et al., "Targeted delivery of antibodies through the blood-brain barrier by MRI-guided focused ultrasound," Biochemical and Biophysical Research Communications, vol. 340, No. 4, Feb. 24, 2006, pp. 1085-1090.
Kooiman et al. Ultrasound-responsive cavitation nuclei for therapy and drug delivery. Ultrasound Med Biol. Jun. 1, 2020;46(6):1296-1325.
Kotopoulis, et al., "Sonoporation with Acoustic Cluster Therapy (ACT®) induces transient tumour volume reduction in a subcutaneous xenograft model of pancreatic ductal adenocarcinoma", J Control Release, Nov. 2026; 245:70-80.
Kurdziel et al., "Human dosimetry and preliminary tumour distribution of 18F-fluoropaclitaxel inhealthy volunteers and newly diagnosed breast cancer patients using PET/CT". J Nucl Med. Sep. 1, 2011;52(9):1339-1345.
Lattwein et al., Sonobactericide: an emerging treatment strategy for bacterial infections. Ultrasound Med Biol. Feb. 1, 2020;46(2):193-215.
Mainprize et al., "Blood-Brain Barrier Opening in Primary Brain Tumors with Non-invasive MR-GuidedFocused Ultrasound: A Clinical Safety and Feasibility Study," Scientific Reports, vol. 9, No. 1, Dec. 1, 2019 in 7 pages.
Miller et al., "Bioeffects Considerations for Diagnostic Ultrasound Contrast Agents", Journal of Ultrasound Med 2008; vol. 27, pp. 611-632.
Ng et al., "Abstract A099: Acoustic Cluster Therapy enhances the efficacy of chemotherapeutic regimens in patient-derived xenograft mouse models for pancreatic ductal adenocarcinoma," Molecular Cancer Therapeutics, vol. 18, Dec. 1, 2019.
Postema et al., "Contrast-enhanced and Targeted Untrasound", World Journal of Gastroenterol, Jan. 7, 2022, vol. 17, pp. 28-41.
Ryman et al., "Pharmacokinetics of monoclonal antibodies". CPT Pharmacometrics Syst Pharmacol. Sep. 2017;6(9):576-588.
Schultz et al., "Selecting the Optimal Parameters for Sonoporation of Pancreatic Cancer in a Pre-Clinical Model," 2019 IEEE International Ultrosonics Symposium (IUS), IEEE, Oct. 6, 2019 (Oct. 6, 2019), pp. 328-331, XP033671248, DOI: 10.1109/ULTSYM.2019.8925889.
Sontum et al., "Acoustic Cluster Therapy (ACT)—A novel concept for ultrasound mediated, targeted drug delivery." Int J Pharma. Nov. 30, 2015;495(2):1019-1027.
Sontum et al., "Acoustic Cluster Therapy—A Novel Approach for Ultrasound Mediated Targeted Drug Delivery: Technology Basics and Proof of Concept". In submitted to 21st European Symposium on Ultrasound Contrast Imaging, Rotterdam, Jan. 21, 2016 (vol. 22); 4 pages.
Timko et al., "Remotely triggerable drug delivery systems", Adv Mater. Nov. 24, 2010;22(44): 4925-4943.
Van Wamel et al., "Acoustic Cluster Therapy (ACT): a novel concept for targeted drug delivery—In vivo Characteristics and Proof of Principle," ResearchGate, Jan. 1, 2015; in 4 pages.
Van Wamel et al. "Acoustic Cluster Therapy (ACT) enhances the therapeutic efficacy of paclitaxel and Abraxane® for treatment of human prostate adenocarcinoma in mice", J Control Rel. Aug. 28, 2016;236:15-21.
Van Wamel et al. "Acoustic Cluster Therapy (ACT)—pre-clinical proof of principle for local drug delivery and enhanced uptake," Journal of Controlled Release, vol. 224, Jan. 13, 2016, pp. 158-164.
Van Wamel et al., Ultrafast microscopy imaging of acoustic clustere therapy bubbles: Activation and oscillation. Ultrasound in Med Biol. Sep. 1, 2022;48(9): 1840-1857.
Wang et al., "Experimental study of tumor therapy mediated by multimodal imaging based on a biological targeting synergistic agent," Intl J Nanomed. Mar. 17, 2020: 1871-1888.
Wei et al., "Focused Ultrasound-Induced Blood-Brain Barrier Opening to Enhance Temozolomide Delivery for Glioblastoma Treatment: A preclinical Study," PLOS ONE, vol. 8, No. 3, Mar. 1, 2013 in 10 pages.
Zhang et al., "Focused-ultrasound Mediated Anti-Alpha-Synuclein Antibody Delivery for the Treatment of Parkinson's Disease," 2018 IEEE International Ultrasonics Symposium, Oct. 22, 2018, pp. 1-4.
Zheng et al., "Targeted microbubbles with ultrasound irradiation and PD-1 inhibitor to increase antitumor activity in B-cell lymphoma," Nanomedicine, vol. 13, No. 3, Feb. 1, 2018, pp. 297-311.
International Search Report and Written Opinion received in PCT Application No. PCT/No. 2023/060084 mailed on Feb. 19, 2024 in 9 pages.
Campbell et al. Lett Appl Microbiol. 2019; 69: abstract. (Year: 2019).
Duck, "Acoustic Dose and Acoustic Dose-Rate", Ultrasound Med. Biol., vol. 35, No. 10, Oct. 2009, pp. 1679-1685.
Liang et al., "Intelligent Nanocomposites with Intrinsic Blood-Brain-Barrier Crossing Ability Designed for Highly Specific MR Imaging and Sonodynamic Therapy of Glioblastoma", Small, vol. 16, No. 8, 2020:e1906985, pp. 1-12.
Liu et al., "Photoacoustic Therapy for Precise Eradication of Glioblastoma with a Tumor Site Blood-Brain Barrier Permeability Upregulating Nanoparticle", Advanced Functional Materials, vol. 29:1808601, Jan. 25, 2019, pp. 1-13.
Lukka et al., "High-intensity Focused Ultrasound for Prostate Cancer: a Systematic Review", Clinical Oncology, vol. 23, 2011, pp. 117-127.
Meakins et al., "Longwave ultrasound and conductive heating increase functional ankle mobility in asymptomatic subjects", Physical Therapy in Sport, vol. 7, Issue 2, May 2006, pp. 74-80.
Postema et al (Contrast-enhanced and targeted ultrasound. World J Gastroenterol Jan. 7, 2011; 17(1): 28-41) (Year: 2011).
Sontum et al., "Acoustic Cluster Therapy—A Novel Approach for Ultrasound Mediated Targeted Drug Delivery: Technology Basics and Proof of Concept," 2016, Department of Physics, NTNU, Trondheim, Norway, Phoenix Solutions AS, Oslo, Norway, Joint Department of Physics, ICR, London, U.K., in 4 pages.
Zhang et al., "Acoustic Droplet Vaporization for Enhancement of Thermal Ablation by High Intensity Focused Ultrasound," Acard Radiol. Sep. 2011;8(9): 1123-1132.

(56) References Cited

OTHER PUBLICATIONS

Sontum et al., "Acoustic Cluster Therapy (ACT)—A novel concept for ultrasound mediated, targeted drug delivery," (Nov. 30, 2015), International Journal of Pharmaceutics, vol. 495, Issue 2, Nov. 30, 2015, pp. 1019-1027. (Year: 2015).

Van Wamel et al., "Acoustic Cluster Therapy (ACT) enhances the therapeutic efficacy of paclitaxel and Abraxane® for treatment of human prostate adenocarcinoma in mice," (Aug. 28, 2016), Journal of Controlled Release, vol. 236, Aug. 28, 2016, pp. 15-21. (Year: 2016).

* cited by examiner

METHOD AND SYSTEM FOR CALCULATING A POINT ESTIMATE OF AN ULTRASOUND DOSE

BACKGROUND

Ultrasound has long been used for diagnostic imaging applications. More recently there has been growing interest and development of the use of ultrasound in conjunction with microbubbles for drug delivery, immunotherapy, blood brain barrier opening, and other applications.

As an ultrasound wave propagates through tissue, the energy of the wave is attenuated through several mechanisms, including scattering and absorption. The absorption mechanism transfers energy from the ultrasound wave to the tissue, wherein the energy is dissipated as heat. Excessive heating of tissue can lead to tissue destruction or other undesirable bioeffects. When using ultrasound for diagnostic purposes such effects should be avoided. Thermal index (TI) is a dimensionless parameter that aims to indicate the level of tissue heating during ultrasound scanning. This index is displayed on diagnostic ultrasound equipment and there is a defined upper bound that should not be exceeded in diagnostic settings.

The combination of high rarefactional pressure and low frequency in an ultrasound wave may lead to a mechanical effect known as cavitation. In cavitation, gas bubbles can form, oscillate, and collapse with varying degrees of violence, and produce unwanted biological effects. Mechanical index (MI) is a dimensionless parameter that indicates the likelihood for cavitation to occur and is often displayed on diagnostic ultrasound instruments. Regulatory requirements during medical ultrasound imaging are to use a MI less than 1.9. During ultrasound imaging with microbubble contrast agents, an MI below 0.7 is recommended to avoid detrimental bio-effects such as micro-haemorrhaging and irreversible vascular damage. During ultrasound imaging with microbubble contrast agents, using an MI below 0.4 is considered "best practice". MI is defined as the peak negative (rarefraction) pressure in the ultrasound field (PNP), de-rated by an attenuation factor to account for in-tissue acoustic attention, divided by the square root of the centre frequency (Fc) of the ultrasound field in MHz, as per the formula below.

$$MI = \frac{P_{r,\alpha} \cdot f_{awf}^{-0.5}}{C_{MI}} \quad \text{Equation 1}$$

wherein $C_{MI} = 1\ \text{Mpa MHz}^{-\frac{1}{2}}$ and is included to provide MI as a dimensionless parameter;

$f_{awf}$ is an acoustic working frequency;

$P_{r,\alpha}$ is an attenuated peak rarefaction pressure; and $\alpha$ is a derated attenuation factor.

An ultrasound pressure amplitude of an ultrasound field produced by a medical ultrasound scanner with a connected ultrasound probe is characterized by immersing a probe face of the ultrasound probe in water and measuring a pressure wave emitted from the probe with a hydrophone. From these measurements, a pressure wave amplitude that the probe can generate in tissue is estimated. To calculate an upper safe operating limit of MI or TI, a conservative value for the ultrasound attenuation of the tissue is used for this estimation. A conservative value of 0.3 dB $cm^{-1}$ $MHz^{-1}$ helps to avoid unwanted bio-effects during diagnostic ultrasound of subjects. However, this is a highly simplified calculation of the MI, which assumes a homogeneous tissue path from the ultrasound source to the target area and is not adequate for ultrasound implementations that require greater accuracy of ultrasound energy delivery.

These current recommendations are not tailored or optimized for ultrasound mediated therapy. For effective deployment of the mechanical and thermal mechanisms of action involved when applying ultrasound irradiation in therapy it is important to have the best estimate of ultrasound dose being delivered to the tissue volume being treated. The invention provides a method for real-time ultrasound dosimetry in ultrasound mediated therapy.

EP2468191 A1 discloses an ultrasound diagnosis apparatus providing a map of an interest index. The ultrasound diagnosis apparatus includes: a calculating unit for calculating a mechanical index (MI) corresponding to a depth value in a direction in which ultrasound travels from an ultrasound output part of a transmission transducer; a visualization unit for generating an MI map in which a relationship between the calculated MI and the depth value is visualized in the form of a graph; and a display unit for displaying the MI map.

EP 2 521 593 B1 discloses a system for applying focused ultrasound energy to a nerve surrounding a blood vessel of a patient, the system comprising: a platform for supporting the patient; one or more piezoelectric arrays coupled to the platform, the one or more piezoelectric arrays comprising a plurality of piezoelectric elements; a controller configured to control the piezoelectric elements; a programmable generator configured to generate output power for one or more of the piezoelectric elements; and a programmable processor configured to process a signal sensed by at least one of the piezoelectric elements: the platform comprises a table with a recess for the one or more piezoelectric arrays; and the one or more of the piezoelectric elements are configured to deliver energies to treat regions around the blood vessel.

WO 2021/118783 A1 discloses techniques for neuromodulation of a tissue that include applying energy (e.g., ultrasound energy) into the tissue al multiple regions of interest, concurrently or consecutively. The neuromodulation may result in tissue displacement, which may be observed through changes in one or more molecules of interest.

Acoustic Cluster Therapy (ACT)—A novel concept for ultrasound mediated, targeted drug delivery, Sontum et al [25 Sep. 2015] discloses a novel approach for ultrasound (US) mediated drug delivery-Acoustic Cluster Therapy (ACT, and basic characteristics of the ACT formulation are elucidated. The concept comprises administration of free flowing clusters of negatively charged microbubbles and positively charged microdroplets. The clusters are activated within the target pathology by diagnostic US, undergo an ensuing liquid-to-gas phase shift and transiently deposit 20-30 μm large bubbles in the microvasculature, occluding blood flow for ~5-10 min. Further application of US will induce biomechanical effects that increases the vascular permeability, leading to a locally enhanced extravasation of components from the vascular compartment (e.g. released or co-administered drugs). Methodologies are detailed for determination of vital in-vitro characteristics of the ACT compound; cluster concentration and size distribution. It is shown how these attributes can be engineered through various formulation parameters, and their significance as predictors of biological behaviour, such as deposit characteristics, is demonstrated by US imaging in a dog model. Furthermore, in-vivo properties of the activated ACT bubbles are studied by intravital microscopy in a rat model, confirming the postulated behaviour of the concept.

SUMMARY OF THE INVENTION

According to a first aspect of the invention there is provided a method for calculating a point estimate of an ultrasound dose at a target treatment area, comprising: calculating a unique ultrasound propagation correction factor for a specific ultrasound propagation path through a particular region of interest by: obtaining a medium property map of the region of interest, wherein the medium property map provides a plurality of different medium property values in different segments of the region of interest dependent on a medium within each of said segments, comprising: obtaining an image of the region of interest, wherein the region of interest comprises a target treatment area and a surrounding region of the target treatment area; processing the image to identify different components of the region of interest; segmenting and categorizing the different components into predetermined media categories; retrieving a medium property value associated with each media category, comprising; estimating a category-specific ultrasound coupling bubble element correction to the medium property value resulting from the presence of at least one ultrasound coupling bubble element in at least one component; and adjusting the medium property value of the at least one component to account for the respective category-specific ultrasound coupling bubble element correction; and attributing said medium property value to each respective component of the segmented region of interest; delineating the propagation path from an ultrasound source to the target treatment region; compiling the medium property values for each segment over the propagation path to calculate the unique propagation correction factor; and using the unique propagation correction factor to indicate the ultrasound dose delivered to the target treatment area.

The media categories may comprise at least one of: different tissue types; different tissue types afflicted by one or more particular diseases; a fluid; and a gas.

The different tissue types comprise one or more of: soft tissue comprising fat, muscle, parenchyma, tendons and ligaments; and hard tissue comprising bone.

Obtaining the image of the region of interest may comprise at least one of: retrieving a pre-scanned scan of the region of interest; taking a pre-scan scan of the region of interest; and using a real-time diagnostic imaging system image.

The scan may comprise one or more of: a computer tomography image; and a magnetic resonance image.

The category-specific medium property values may be retrieved from a database.

The at least one ultrasound coupling bubble element may comprises one or more of: contrast agent microbubbles; cavitation seeds, large microbubbles; ACT® bubble technology ultrasound coupling bubble elements, wherein the ACT® bubble technology ultrasound coupling bubble elements comprise: ACT® microbubble clusters; and activated ACT® bubbles.

The at least one ultrasound coupling bubble element may comprise contrast agent microbubbles and wherein estimating a contrast agent microbubble correction comprises: retrieving or estimating one or more contrast agent microbubble parameters, wherein the one or more contrast agent microbubble parameters comprise: a value for the dose of contrast agent microbubbles administered; contrast agent characteristics per unit concentration; a blood volume of the subject; a cardiac output of the subject; a value of blood volume associated with each category; arrival times after intravenous administration of the contrast agent for each category; and a time concentration curve; and using the contrast agent parameters to calculate the contrast agent correction for each category.

The at least one ultrasound coupling bubble element may comprise ACT® bubble technology ultrasound coupling bubble elements and wherein calculating an additional ACT® bubble correction comprises: estimating additional correction resulting from ACT® microbubble clusters in the presence of the high frequency activation ultrasound; estimating additional correction resulting from generated ACT® bubbles in the presence of high frequency activation ultrasound; and estimating additional correction resulting from ACT® bubbles in the presence of low frequency enhancement ultrasound.

Calculating additional ACT® bubble correction may further comprise: estimating a number of ACT® bubbles in the categories associated with each component by: retrieving or estimating one or more ACT® bubble parameters, wherein the ACT® bubble parameters comprise: a blood volume of the subject; a cardiac output of the subject; a perfusion of each category of components; and a time concentration curve; and calculating the number of ACT® bubbles delivered to each of the components by multiplying a fraction of the cardiac output that accounts for the perfusion of each category of components by a yield of activation of ACT® bubble clusters.

The estimation of the number of ACT® bubbles in the categories associated with each segment may comprise a time dependency by: retrieving a value for a lifetime of an ACT® bubble in each category to model a reduction of the number of ACT® bubbles in each category over time.

Calculating the correction resulting from the presence of contrast agent in each category may be based on contrast mode imaging ultrasound.

Calculating the additional correction resulting from the presence of ACT® bubbles in each category may be based on fundamental B-mode imaging ultrasound.

The method may further comprise using the unique propagation correction factor to calculate at least one of a resulting pressure, a resulting mechanical index, a resulting intensity, a resulting power and a resulting thermal index, which are indications of delivered ultrasound dose.

According to a second aspect of the invention, there is provided a non-transitory computer-readable storage medium, the computer-readable storage medium having stored thereon instructions that when executed on a processor perform the method of the first aspect of the invention.

According to a third aspect of the invention there is provided a system for providing a point estimate of an ultrasound dose at a region of interest in a subject comprising: an ultrasound source; an image processor module for processing images to identify different components of the region of interest; a computer processor; a database module comprising medium property values associated with a plurality of categories for components within the region of interest; a data storage module comprising computer readable instruction that when executed on the processor perform the tasks of: retrieving an image of the region of interest, wherein the region of interest comprises a target treatment area and a surrounding region of the target treatment area; processing the image to identify different components of the region of interest; segmenting and categorizing the different components into predetermined media categories; retrieving a medium property value associated with each media category, comprising; estimating a category-specific ultrasound coupling bubble element correction to the medium property value resulting from the presence of at least one ultrasound coupling bubble element in at least one component; and adjusting the medium property value of the at least one component to account for the respective category-specific ultrasound coupling bubble element correction; and attributing said medium property value to each respective component of the segmented region of interest; delineating an ultrasound propagation path from the ultrasound source to the target treatment region; compiling the medium property values for each component over the propagation path to calculate an ultrasound propagation correction factor unique to the ultrasound propagation path through the region of interest; calculating the point estimate of the ultrasound dose at the region of interest based on the unique propagation correction factor; and adjusting the ultrasound source according to the calculated point estimate of the ultrasound dose if outside of a predetermined ultrasound dose range.

According to a fourth aspect of the invention, there is provided a system for providing a point estimate of an ultrasound dose at a region of interest in a subject comprising: an ultrasound source; an image processor module for processing images to identify different components of the region of interest; a computer processor; a database module comprising medium property values associated with a plurality of categories for components within the region of interest; a data storage module comprising computer readable instruction that when executed on the processor perform the tasks of: delineating an ultrasound propagation path from the ultrasound source to the target treatment region; compiling the medium property values for each component over the propagation path to calculate an ultrasound propagation correction factor unique to the ultrasound propagation path through the region of interest; calculating the point estimate of the ultrasound dose at the region of interest based on the unique propagation correction factor; and adjusting the ultrasound source according to the calculated point estimate of the ultrasound dose if outside of a predetermined ultrasound dose range.

The image processor may be configured to segment and categorize the different components of the region of interest by: identifying boundaries between different patterns of the image; analysing the pattern within the boundaries; and comparing each of the patterns to image patterns of known tissue type to find a match.

The system may be a machine learning system and wherein each processed image, along with associated image data, is accumulated as training data to provide more accurate segmentation and categorization by the image processor over time.

The system may be further configured to: track the probe position; re-evaluate one or more propagation correction factors with movement of the probe position; and store a one or more propagation correction factors per probe position to reduce a computational load.

The system may be further configured to: track an in-plane and out-of-plane rhythmic movement of the medium of the region of interest; re-evaluate one or more propagation correction factors for each in-plane and out-of-plane position of the moving medium; and store the one or more propagation correction factors for each in-plane and out-of-plane position of the moving medium.

The system may be configured to track the in-plane and out-of-plane rhythmic movement of the medium through speckle-tracking or machine learning algorithms.

The method of the first aspect or the second aspect or the system of the fourth aspect, wherein the medium property may comprise at least one of attenuation, sound speed, shear wave velocity, acoustic impedance, coefficients of non-linear compressibility, and coefficients of dispersion.

The medium property may further comprise one or more derived properties that can be derived from any one, or any combination, of the medium properties listed.

DETAILED DESCRIPTION

Figure 1:
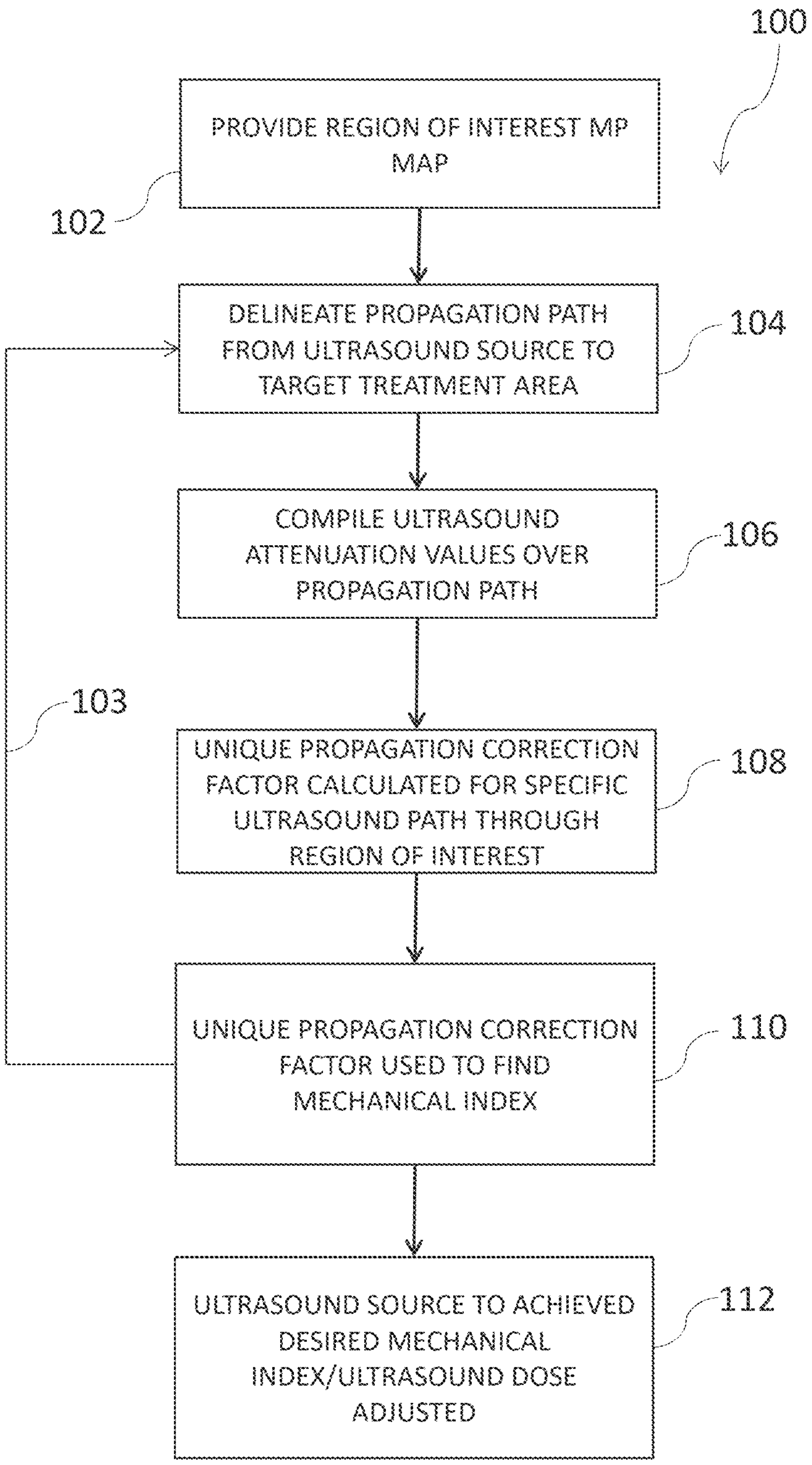
FIG. 1 is a flow chart of a method for calculating a point estimate of an ultrasound dose.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

As used herein, the term “ultrasound dosimetry” in the field of medical ultrasound technology describes the determining, such as measurement, calculation and assessment of an ultrasound radiation dose to be delivered to a target tissue to achieve sought bioeffects.

As used herein, the term “ultrasound irradiation” or “insonation” describes exposure to, or treatment with, ultrasound.

As used herein, the term “sound speed” refers to group velocity and/or phase velocity and/or signal velocity of a longitudinal pressure wave.

As used herein, the term "ultrasound dose" or "ultrasound dosage" refers to instantaneous, time-averaged, spatially averaged, time integrated, and spatially integrated ultrasound parameters in a point or region, for example as parameters defined in international standards for medical diagnostic ultrasound fields IEC62127-1, IEC62359, IEC60601-2-37.

As used herein, the terms 'ACT bubble' or 'ACT® bubble' are used interchangeably and refer to large, activated bubbles derived from the ACT microbubble clusters after insonation by activation ultrasound.

In diagnostic imaging applications there are a number of acoustic parameters that are used to quantify various aspects of the ultrasound dose being applied, such as the mechanical index (MI), thermal index (TI), intensity spatial peak temporal average (Ispta), among others. Typically, therapeutic and diagnostic ultrasound treatment involves ultrasound irradiation of a region of interest of a subject with a predefined ultrasound dosage delivered by a transducer positioned at, or towards, the region of interest.

The use of ultrasound technology alone or in conjunction with contrast agents, such as microbubble compositions, for diagnostic applications is well established. There is now a growing interest and development of the use of ultrasound for therapeutic applications. There is a need for ultrasound dosimetry for ultrasound and microbubble mediated delivery of drugs, ultrasound and microbubble mediated therapy, and ultrasound mediated therapy. For effective deployment of the mechanical and thermal mechanisms of action involved when applying ultrasound irradiation in therapy, it is important to have a best estimate of an ultrasound dose being delivered to the tissue volume being treated.

A real ultrasound dose (point estimate of an ultrasound dose) delivered to a target region by an ultrasound source is dependent on the configuration of the source and ultrasound transmission parameters and properties that are characteristic of the media through which the ultrasound propagates from the source to the target region. Thus, propagation through various tissue types and the presence of one ultrasound coupling bubble elements may alter ultrasound wave parameters, for example the frequency, a wavefront phase and an amplitude, and thus impacts the true ultrasound dose at the target region.

The invention comprises identifying and segmenting various tissue types in a region of interest, estimating the presence of at least one ultrasound coupling bubble element (e.g., microbubbles and/or ACT® bubbles) in each of said various tissue types and calculating at least one propagation correction factor for use in calculating a more accurate ultrasound dose, and optionally and reconfiguring an ultrasound source that provides the ultrasound dose.

The ultrasound coupling bubble element may be contrast agent microbubbles, ACT® microbubble clusters, cavitation seed type agents, large bubbles and/or activated ACT® bubbles. In other words, an ultrasound coupling bubble element is a microbubble technology. Large bubbles of microbubble technologies have a diameter of more than 8 μm and can be trapped in a capillary bed of the subject.

Acoustic Cluster Therapy (ACT®) is a technology for ultrasound-mediated, localized drug delivery. ACT® comprises negatively charged microbubbles containing perfluorobutane (PFB), stabilized by a monomolecular phospholipid membrane, combined with positively charged microdroplets also stabilized by a monomolecular phospholipid membrane containing perfluoromethylcyclopentane (PFMCP). Mixing these microbubbles and microdroplets forms small clusters held together by electrostatic forces. The ACT® microclusters may be co-administered with a therapeutic drug. When insonated with pulsed ultrasound (typically in the clinical diagnostic regime and frequency 2-5 MHZ), these clusters undergo an activation step, causing oscillating microbubbles to transfer energy to the microdroplets, leading to an instant vaporization of the microdroplets which forms larger bubbles, hereafter referred to as ACT® bubbles.

Spatially varying properties of the media in the region through which the ultrasound propagates, comprise: attenuation, sound speed, shear wave velocity, acoustic impedance, coefficients of non-linear compressibility, and coefficients of dispersion. The at least one propagation correction factor can be calculated based on one or more of said properties or derivatives thereof.

The ultrasound dose is determined based on one or more of the established ultrasound parameters as defined in IEC62127-1, IEC62359, IEC60601-2-37, such as, for example: peak negative pressure, peak positive pressure, mechanical index (MI), thermal index (TI), spatial peak temporal average intensity (Ispta), spatial peak pulse average intensity (Ipa), spatial average temporal average intensity (Isata), and total acoustic power.

FIG. 1 is a flow chart of a method 100 for calculating a point estimate of an ultrasound dose.

The method starts at 102 wherein a media property (MP) map of a region of interest of a subject is obtained, wherein the MP map provides specific and differing MP values across the region of interest. The MP map is based on a specific constitution and anatomy of the region of interest and/or the presence of other constituents. The MP map and an example method of how it is obtained is described in more detail below with respect to FIG. 2.

An example MP map is an attenuation map wherein the attenuation map provides specific and differing attenuation values across the region of interest, said attenuation values based on a specific constitution and anatomy of the region of interest and the presence of other constituents, in particular the presence of one or more ultrasound coupling bubble elements. Another example MP map is a sound speed map wherein changing mass density and bulk modulus of the changing medium through which ultrasound is traveling affects the sound speed of the ultrasound wave. The sound speed map provides specific and differing sound speed values across the region of interest, said sound speed values based on a specific constitution and anatomy of the region of interest and the presence of other constituents. A further example is a phase map which may be a combination of the sound speed map and an attenuation map. In a preferred embodiment, two or more of the individual MP maps for attenuation, sound speed, non-linear coefficient and phase are combined to provide a combined media properties (CMP) map of the region of interest.

At 104, a dose defining propagation path (PP) is approximated (projected). In a first example, this is achieved by delineating a line-of-sight from the source to the target tissue. Alternatively, this is achieved by tracing multiple lines-of-sight each originating from each of the elements in a transducer array. In a preferred example, the PP is an acoustic model of a transmitted ultrasound field. Ultrasound is usually applied on an external or an internal surface of the body or generated inside the body by insertion of the transducer e.g., via a laparoscope. The ultrasound waves will experience different absorption, scattering, refraction and aberration as the waves traverse each component along the path.

At 106, a computation (i.e., integration) of the MP values over the PP can be taken to calculate 108 the unique propagation correction factor (PCF) of the PP through the particular region of interest. In some examples the PCF is complex valued.

At 110, a resultant MI or TI from the ultrasound field along the PP is estimated based on a preselected set of ultrasound parameters and the PCF.

The preselected set of ultrasound parameters may be modified based on the initial MI or TI estimate and used along with the PCF to give an improved/refined MI/TI estimate.

Further optimised parameter sets can be used along with the PCF to converge to an optimal estimate of the MI/TI, in an iterative manner. Since the attenuated temporal peak rarefaction pressure $P_{r,\alpha}$ can be defined in any point of the ultrasound field transmitted by the source by:

$$P_{r,\alpha} = P_r \cdot 10^{-\alpha/20} \qquad \text{Equation 2}$$

The optimal MI can be calculated using a modified version of Equation 1 wherein α is substituted for the attenuation correction factor ($\alpha_{CF}$)

$$\alpha \rightarrow \alpha_{CF} \qquad \text{Equation 3}$$

and $$\alpha_{CF} = \sum_{i=1}^{N_t} \Delta d_i \cdot \alpha_i$$

wherein $N_t$ is a number of different tissue types between the transducer and target depth, $\alpha d_i$ is a tissue layer thickness in unit depth of the respective tissue type i, and $\alpha_i$ is a tissue layer attenuation coefficient per unit depth in dB/unit depth. Alternatively, the attenuation coefficient may be modelled as a spatially varying function $\alpha_r(\vec{r})$ where $\vec{r}$ is the spatial position so that $$\alpha_{CF} = \int_{PP}^{\square} \alpha_r(\vec{r}) d\vec{r}. \qquad \text{Equation 4}$$

Thus, in the example wherein the PCF is an attenuation correction factor, the attenuation correction factor may be used in the adjusted equation relating said attenuation factor, an ultrasound working frequency and the mechanical index:

$$MI = \frac{P_{r,\alpha_{CF}} \cdot f_{awf}^{-0.5}}{C_{MI}} \qquad \text{Equation 5}$$

$$\text{wherein } C_{MI} = 1\ \text{MPa}\,\text{MHz}^{-\frac{1}{2}}$$

and is included to provide MI as a dimensionless parameter, $f_{awf}$ is the acoustic working frequency; and $P_{r,\alpha_{CF}}$ is the attenuated temporal peak rarefaction pressure at the target region dependent on the attenuation correction factor.

At 112, the calculated MI may be transmitted to an ultrasound source to automatically adjust the output settings of the ultrasound source in order to deliver a specialized ultrasound dose to a tissue volume to be treated. Alternatively, the MI may be displayed and a user may manually adjust the settings of the ultrasound source wherein the displayed MI value is calculated and updated in real-time via method 100.

Steps 104 to 110 can be performed in a continuous loop 103, in real-time, during ultrasound imaging and/or therapy. For example, if the ultrasound source/transducer is moved, the PP changes and the PCF is recalculated. Movement of the ultrasound source may be detected using hardware and software for spatial tracking of one or more of a movement, orientation and attitude of the ultrasound source. Such tracking can also be combined with co-registered images from other imaging modalities, including CT and MRI. In a further example the PCF is recalculated when the region of interest is moved by other external factors, such as subject movement or breathing motion.

In an example, the PCF is determined by an attenuation correction factor and a phase change correction factor. In this case, the steps 104 to 110 can be performed in a continuous loop, in real-time, during ultrasound imaging and/or therapy. For each loop iteration, one of the factors is recalculated based on an image-specific metric, for example the point spread function of a single point scatterer in a region of interest. An example of such a point scatterer is an activated ACT® cluster.

Figure 2:
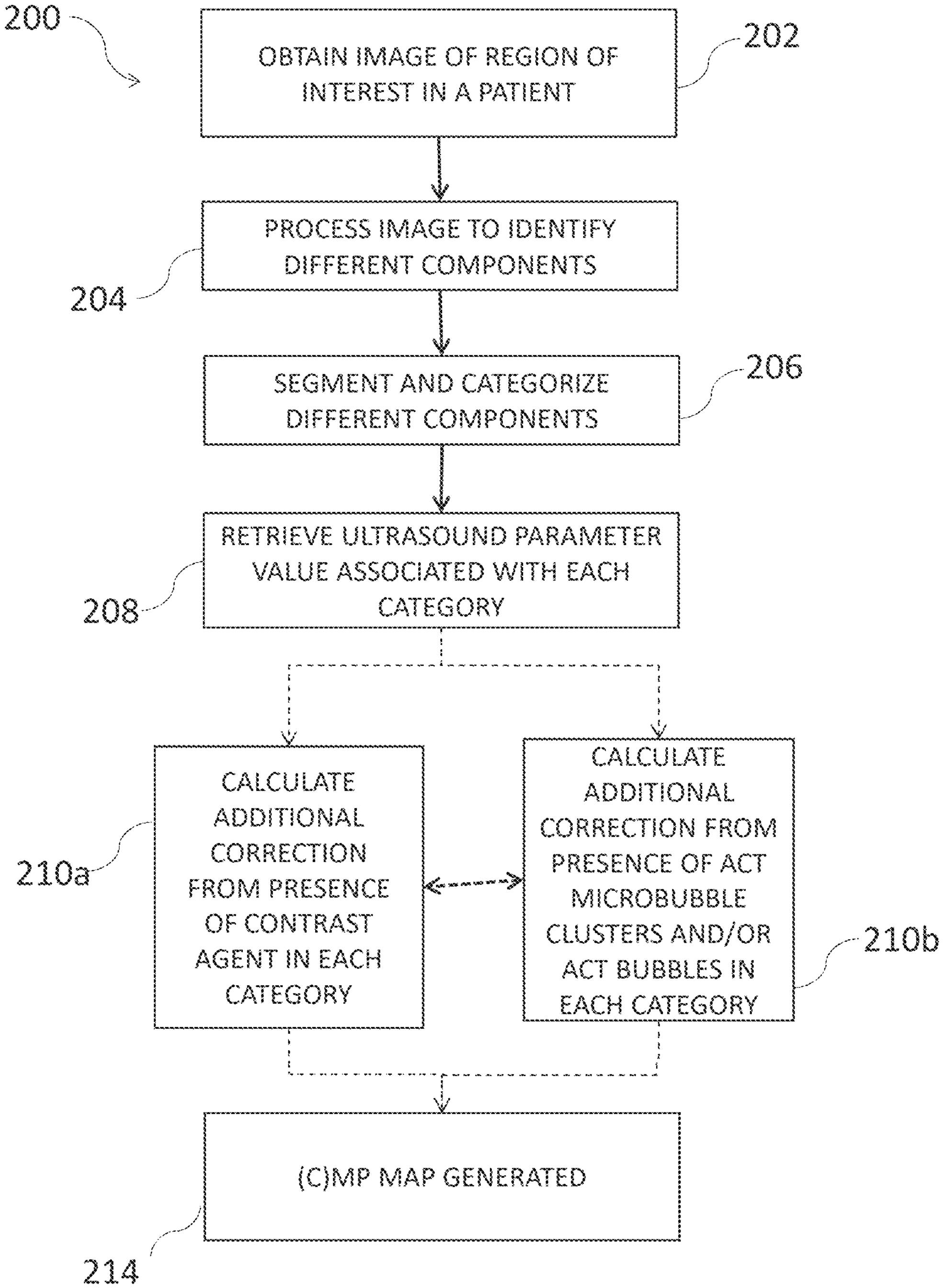
FIG. 2 is a flow chart of a method for calculating a media proprieties map of a region of interest.

FIG. 2 is a flow chart of method 200 for creating a unique (C) MP map for a particular region of interest. Method 200 provides step 102 of method 100. The (C) MP map is comprised of segments of known volume/area with an associated MP value for each segment. The MP map may be an attenuation map, a sound speed map, a shear wave velocity map, an acoustic impedance map, a dispersion coefficient map, a non-linear coefficient map, or a map of a parameter derived from these properties. The MP map may be a CMP combining two or more of the above maps.

At 202, an image of a region of interest in a subject is obtained. The region of interest is a target area and a surrounding area to the target area. The target area is the area in which the ultrasound dose is to be delivered. For example, the target area may be a metastasis in a liver of a subject and the surrounding area may be healthy liver, muscle, fat and other neighbouring organs. The image of the region of interest may be obtainable in various different ways. For example, many images of the region of interest may have already been taken during an investigation stage of the health of the subject. Preferably, the image of the region of interest uses 3D imaging data, however, use of 2D imaging data is also possible.

There may already exist scans, in particular volume scans, of the region of interest, for example, magnetic resonance imaging (MRI), computerised tomography (CT) or earlier ultrasound scans which can provide the image of the region of interest in the method 100. Alternatively, new scans, for example MRI or CT scans, of the region of interest may be taken to provide the images of the region of interest. Another method of obtaining an image of the region of interest is to utilise the ultrasound source. The ultrasound source which is used in the method 100 may first be used to obtain an ultrasound scan of the region of interest by insonating the region of interest. The pressure amplitude of the ultrasound waves for the purpose of obtaining the image of the region of interest may be that determined by the conservative derating factor of 0.3 dB $cm^{-1}$ $MHz^{-1}$ to avoid overexposure, before the method to find an accurate estimation of the radiation dose has been calculated. In some examples, the ultrasound scan is obtained in real-time. In a yet further example, the real-time ultrasound scan is superimposed over the pre-scanned image to enhance the information of the region of interest. The imaging may include a step of identifying the target volume, if not already know. The imaging may include the yet further step of identifying tumours or metastasis in the target area.

Figure 3A:
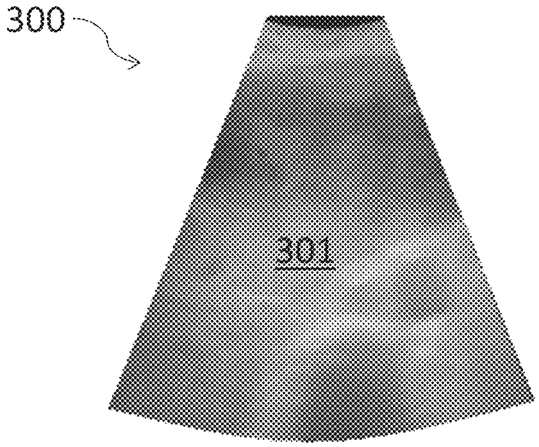
FIG. 3*a* is an example image of a region of interest of a subject.

With reference to FIG. 3*a*, an example image 300 of a region of interest 301 of a subject is shown and is an example of the image that is to be processed by an image processor. The image in the example of FIG. 3*a* was obtained via an ultrasound scan.

At 204, image processing is performed on the image of the region of interest to identify different components and segment the image into different categories 206 based on the identified components. The components to be identified and categorised may be different tissue type in both a healthy state and a diseased state. The different tissue types may include soft tissue such as fat, muscle, tendons and ligaments, and hard tissues such as bone, to name a few non-limiting examples. Metastases may also be identified and categorised differently to other components. The region of interest is segmented in this way since each component may affect the ultrasound waves differently.

Figure 3B:
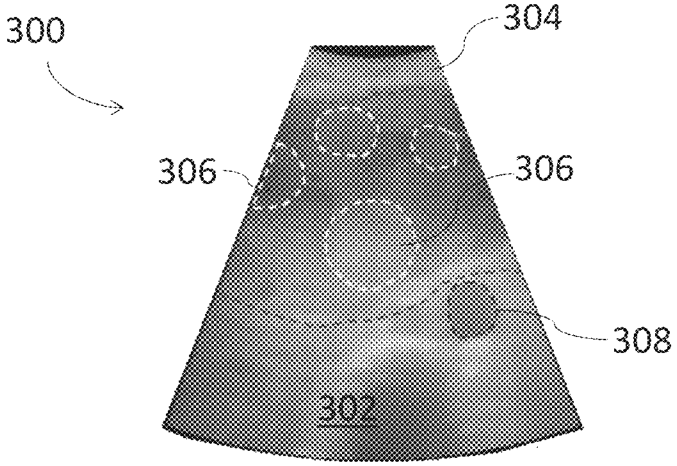
FIG. 3*b* is the example image of the region of interest of FIG. 3*a* with different components identified.

FIG. 3*b* is the example image 300 of the region of interest 301 of FIG. 3*a* segmented into different components by the image processor. In the example of FIG. 3*b*, the identified components are muscle 304, metastases 306, healthy liver 302 and an aorta 308.

At 208, for each component in the region of interest, at least one of the components' associated category specific MP values, for example attenuation and/or sound speed, is retrieved from a database and attributed to that component. An example database is shown below in Table 1.

TABLE 1

| 1 | Tissue | Skin | Muscle | Fat | Parenchyma | Pancreas |
|---|---|---|---|---|---|---|
| 2 | Attenuation 0.5 MHz [dB/cm] | 0.91 | 0.31 | 0.35 | 0.29 | 0.42 |
| 3 | Attenuation 2 MHz [dB/cm] | 3.65 | 1.23 | 1.4 | 1.16 | 1.66 |

Figure 3C:
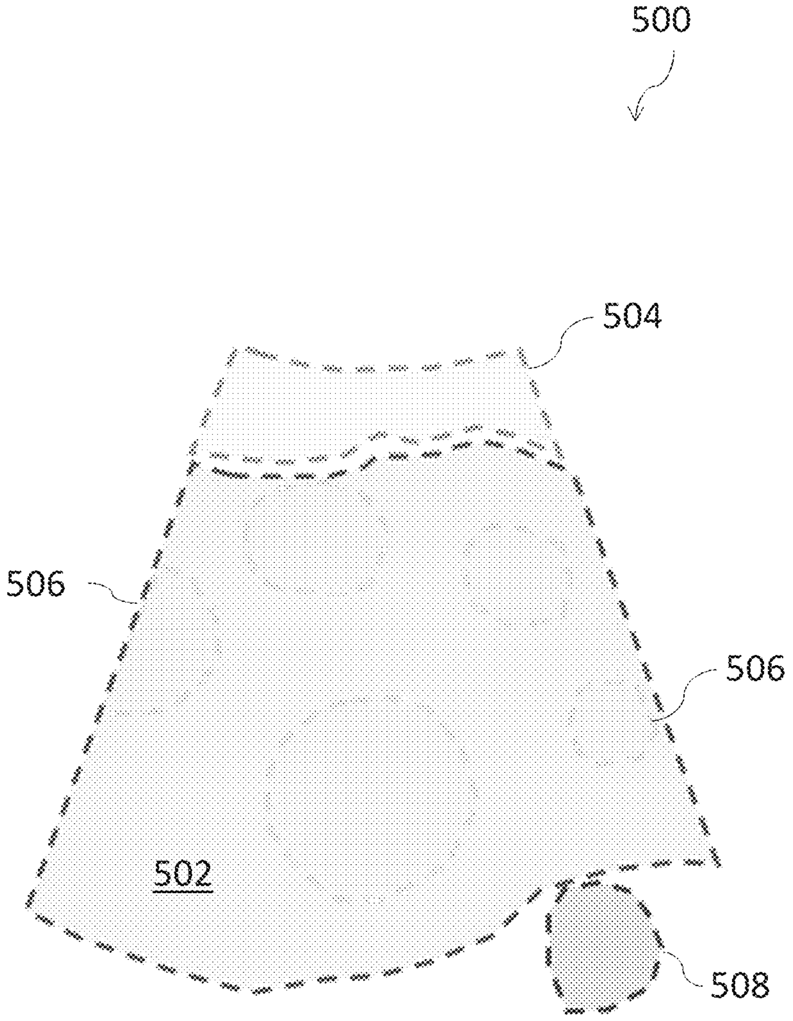
FIG. 3*c* shows a representation of the region of interest made up of identified components.

FIG. 3*c* shows an example MP map in the form of an example attenuation map 500 of the region of interest 301 made up of its component constituents only. Attenuation map 500 is a graphical representation of a collection of data points including 3D/2D coordinates of each of the segments along with respective attenuation values within these segment coordinates. The attenuation map 500 is split into a segment representing a region of healthy liver 502, a segment representing a region of muscle 504, several segments of regions of metastases 506 and a segment representing a region of an aorta 508. The attenuation map 500, may be stored in a database for access by ultrasound scanner software. The attenuation map may be stored in long or short term data storage memory for later retrieval.

The method incorporates a correction 210 to the unique PCF from the presence of one or more ultrasound coupling bubble element in at least some of the tissue layers.

In the particular example of FIG. 2, at step 210*a*, a correction to the PCF is calculated based on the presence of microbubbles, for example contrast agent microbubbles in at least one of the components in the region of interest.

Contrast agent microbubbles are often present in tissue in the region of interest when treating metastases with ultrasound since the contrast agent is often added in a prior ultrasound image capture stage. The addition of the contrast agent to the region alters the acoustic properties of the region. Depending on a frequency of the ultrasound scattering, absorption, reflection, and refraction properties of the region may be altered. For example, a drop in density on the interface between the contrast agent and the surrounding tissue strongly scatters and reflects the ultrasound back to an ultrasound probe. This acoustic property is known as backscattering and results in a higher contrast of different regions on the captured ultrasound image. Since the contrast agent alters the acoustic properties of the region, it may have a significant effect on the derating factor applied to the ultrasound pulses being delivered to the target area. Thus, an additional correction for the contrast agent, and amount thereof, is required to refine the estimate of the ultrasound dose being delivered to the target area. There are at least four commercially available diagnostic ultrasound imaging (contrast) agents on the market; Sonazoid™, Definity™, Optison™ and SonoVue™, which are also being used in clinical studies for therapy applications. These agents are 'free flow' tracers, as they are small enough to circulate in the blood stream and not become trapped in capillaries. The term 'microbubble' or 'regular, contrast microbubble' is used in this text to describe microbubbles with a diameter in the range from 0.2 to 10 μm, typically with a mean diameter between 2 to 3 μm. Other microbubble technologies are also migrating to the clinic such as Acoustic Cluster Therapy® (Exact Therapeutics®) and SonoTrans™ (Oxsonics™).

In the particular example wherein the correction factor is an attenuation correction factor, to calculate the additional attenuation due to the presence of the contrast agent, in terms of attenuation per unit concentration, contrast agent characteristics may be calculated or retrieved from in-vivo experiments. For example, the in-vivo environment may be in whole blood or 5% human serum albumin at 37° C. and at 85% gas saturation. Ultrasound waves at a predetermined frequency are then applied to the environment containing contrast agent. The MI exerted on the environment can be measured. The measured MI and the applied ultrasound frequency can be used to calculate the attenuation per unit concentration of contrast agent microbubbles.

Next, a blood volume of the subject is approximated, for example a 70 kg subject has approximately 5 litres of blood. A cardiac output of the subject is then estimated, for example 5 litres of blood per minute for said 70 kg subject. Estimation of typical values of blood volume not in large compliant vessels is also required for each of the segmented tissue types. For example, the liver has approximately 15% blood volume, and skeletal muscle, skin and adipose tissue at rest have only a fraction of percentage blood volume in comparison to the liver. A table of typical arrival time after intravenous administration of the contrast agent for each component category is then required. A further table of concentration time curves for free-flowing contrast agent administered intravenously is required for each component category. Tables providing values for concentration time curves for free-flowing contrast agent administered intravenously can be found in the art.

Figure 4A:
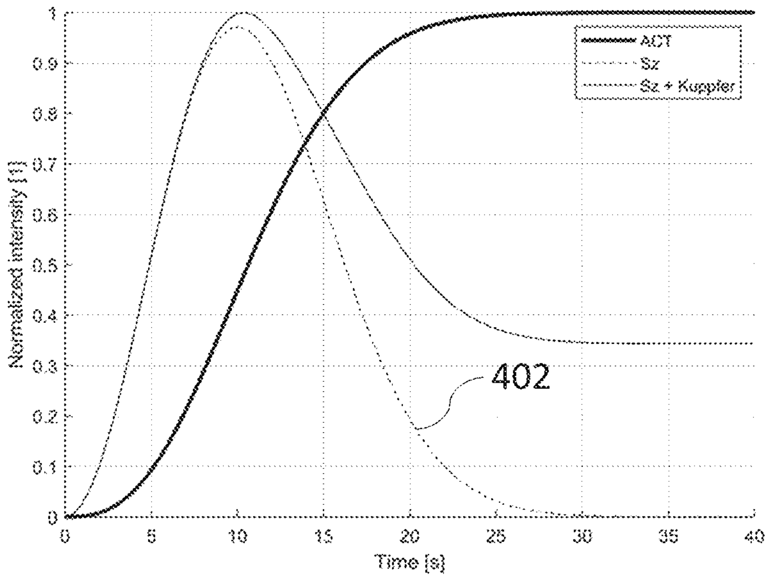
FIG. 4*a* is a graph of normalized backscatter intensity curves of bubbles in a human liver.
Figure 4B:
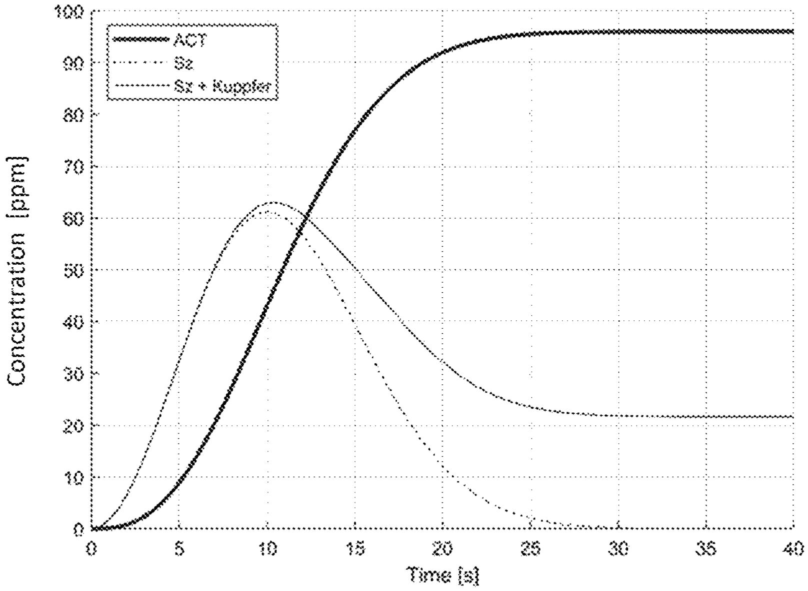
FIG. 4*b* is a graph of concentration of the parenchyma as a function of time, employing the backscatter intensity curves of FIG. 5*a;*

The dynamics of the bubble inflow and wash-out from various organs is well-known for free-flowing microbubbles and has been studied for the activated ACT® bubbles as well. For example, in a dog model the ACT® bubble half-time as measured by the backscatter intensity of ultrasound imaging was 70 seconds. FIG. 4*a* shows typical normalized backscatter intensity curves of the free-flowing microbubble Sonazoid and the ACT® bubbles in the human liver. The ACT® bubbles accumulate in the liver over time as they are activated. The Sonazoid inflow is more rapid and is rapidly reduced due to partial wash-out of the bubbles from the liver. Some of the bubbles are taken up by Kuppfer cells in the liver, which gives a residual concentration after the washout is complete. Similar curves may be created for other organs, in which case the absence of Kuppfer cells causes the free-flowing component of the ACT® injection to follow the dashed line 402. FIG. 4*b* shows a concentration of the parenchyma as a function of time, employing the backscatter intensity curves of FIG. 4*a*. The attenuation in each tissue type will be dependent on time-varying curves such as these. These curves can be determined beforehand, or calculated for each patient by, for example, using the injection duration, T, and the tissue-specific wash-out time, 0, to parameterize a tissue-type specific function on the form $$c_{FF} = c_{FF}^{Peak}(t/\delta\tau)^2\exp(1-(t/\delta\tau)^2),\ \delta\tau = \tau - \theta \quad \text{Equation 6}$$

Similarly, by approximation of the integration of the above $$c_{ACT} = c_{ACT}^{Peak}/(1+\exp(-\delta\tau/2)) \quad \text{Equation 7}$$

These models may also be used as parametrized models in a model-based estimation scheme wherein the parameters are estimated based on the backscatter information that is collected from each segment during the treatment procedure, and on the a priori model for the concentration. The calculated concentration is used to calculate the attenuation experienced by the ultrasound pulse as it transverses the tissue structures between the probe and the target tissue for each time point. For each time point, the configuration of the ultrasound source is updated so that the desired in-situ mechanical index in the target lesion is achieved, for example by adjusting the amplitude or frequency of the excitation of the source.

Thus, from the values of attenuation per unit concentration, blood volume, arrival time after administration, and concentration over time in each component category, the additional attenuation from the presence of contrast agent can be calculated and added to at least one category attenuation value, preferably each category attenuation value associated with a component a concentration of contrast agent.

The peak additional attenuation of the ultrasound pulses that arises from the contrast agent microbubbles is calculated from the data provided in the database. The peak attenuation from free-flowing contrast agent microbubbles can be approximated by using a formula to calculate the concentration of the free-flowing bubbles for each tissue type. Using the patient's body weight, M, the contrast agent injection dose per body weight, D, cardiac output, Q, organ blood volume fraction, $R_B$, injection duration, T, and activation efficiency, n, the peak dose can be calculated as $$c_{FF}^{Peak} = (1-\eta)DMR_B/(\tau Q) \quad \text{Equation 8}$$

After calculation of the correction as a result of contrast agent presence, the method can then advance to step 214, wherein the MP map of the region of interest is generated.

Alternatively or in addition, the method can advance to step 210*b* such that (further) additional correction from the presence of Acoustic Cluster Therapy (ACT®) bubbles in at least one category is accounted for.

In ACT®, small clusters of charged microbubbles that attach to oppositely charged droplets of oil, are injected into the bloodstream. Ultrasound is applied to cause the microbubble to vibrate and transfer energy to the cluster, causing the particles in the cluster to fuse into a single particle. The oil then evaporates into the gas contributed by the microbubble, producing an enlarged microbubble (ACT® bubble). Ultrasonic pulses applied to the ACT® bubbles cause the large gas ACT® bubbles to vibrate.

More specifically, the formulation is a cluster dispersion of microdroplets, having a median diameter of 2 to 3 μm, stabilised with a lipid membrane with a net positive surface charge, forming clusters with microbubbles, having a median diameter of 2 to 3 μm, and stabilised with a lipid shell with a negative surface charge. It is the opposite charge on the oil droplet and microbubble surfaces, respectively, which enable small clusters to be formed via electrostatic interactions. These clusters are of around 5 μm in diameter and are free flowing in the vasculature. When exposed to medical diagnostic ultrasound frequencies the microbubble(s) in the cluster oscillate and the particles fuse into a single entity and the oil evaporates producing the enlarged microbubble (ACT® bubble).

The frequency of the medical diagnostic ultrasound is in the range of 1 to 15 MHz, preferably 2 to 10 MHZ, more preferably 5 MHz. The process of oil droplet-microbubble fusion may be produced even with short imaging pulses, low MI, for example an MI of less than 0.1, and low duty cycles which are typically used in medical imaging systems. Once fused the oil droplets evaporate into the gas that formed the bubble core and a resulting bubble of 20 to 30 μm median diameter is formed. The oil has low water solubility and low diffusion lengths which allow the bubble to persist for several minutes before dissolving. Upon intravenous administration the clusters flow in the blood stream and the large ACT® bubbles are formed (activated) from the clusters where ultrasound fields are applied (activation ultrasound), spatially localising their creation only in the tissue being irradiated with ultrasound. The ACT® bubbles are large enough to trap in the first capillary bed they flow into and become lodged for several minutes. During this time, a lower frequency ultrasound field (enhancement ultrasound) is applied at low MI to drive mechanical oscillations that drive biomechanical mechanisms of action which may produce a therapy effect and/or enhance extravasation and delivery of drugs. The lower frequency of the applied ultrasound field is between 0.1 and 1 MHz, preferably 0.3 to 0.6 MHZ, more preferably 0.5 MHz.

The MI is preferably in the range of 0.1 to 0.4. Thus, for therapy with the ACT® technology, both the ultrasound fields that produce the ACT® bubbles from the clusters at high frequency (activation ultrasound) and the low frequency that drives the mechanical effects for therapy (enhancement ultrasound) both need to be adequately controlled to achieve optimum therapy effects.

Since the applied ultrasound dose for ACT® therapy requires a certain lower limit of energy and unwanted bioeffects and tissue damage must still be controlled, estimation of an accurate ultrasound dose is especially important for ACT® therapy. For example, the conservative lower bound derating factor in current ultrasound control standards may not provide adequate ACT® therapy results and the need for region of interest specific PCF is particularly useful for ACT® therapy.

Since the activation ultrasound is of high frequency and the enhancement ultrasound is of low frequency, there are three elements of the ACT® therapy process, which may separately affect the medium property (i.e., attenuation, sound speed, shear wave velocity, acoustic impedance, coefficients of non-linear compressibility, and coefficients of dispersion, of segments of the region of interest). Thus, an MP correction is preferably calculated for each element. The first element is microbubbles in the presence of the high frequency activation ultrasound. The second element is generated ACT® bubbles in the presence of high frequency activation ultrasound. The third element is ACT® bubbles in the presence of low frequency enhancement ultrasound. An MP correction for each component category is preferably calculated for each of the three elements described above. Hence for ACT® therapy treatment corrections for both the tissue type, number of free-flowing microbubbles and the generation of ACT® bubbles and their lifetime, can all be potentially corrected to alter the ultrasound dosimetry parameters during both the high frequency ultrasound activation step and the low frequency ultrasound therapy enhancement step.

An optional intermediary step in the process of calculating additional MP correction due to ACT® bubbles, is to destroy free-flowing microbubbles with high amplitude and power diagnostic imaging pulses. These high amplitude and power diagnostic imaging pulses may be incorporated in diagnostic scanners as a 'flash' sequence, or part of a 'decorrelation' imaging mode. Such pulses typically have an MI of 0.7 and above. Such pulses can be used to more effectively image the free-flowing microbubble component, or to remove free-flowing microbubbles in the scan plane or tissue volume. Such high intensity pulses do not, however, destroy the ACT® bubbles. Thus, these imaging pulses may be used to clear the free-flowing microbubble component while leaving the ACT® bubble component unaffected. Thus, a need for MP correction due to contrast agent presences can be reduce or even eliminated. For example, the attenuation component from the free-flowing microbubbles may be up to completely removed by destroying practically all of the free-flowing microbubbles prior to insonation of the therapeutic ultrasound dose to the treatment area.

In order to calculate ACT® bubble-related MP correction, first, the number of ACT® bubbles trapped in capillaries is estimated. Values for the total blood volume and the cardiac output of the subject are estimated or retrieved. Then, an estimate of a perfusion rate for each component category is calculated. A number of ACT® bubbles delivered to the tissue can then be calculated by the fraction of the cardiac output that accounts for the perfusion of the tissue type multiplied by a yield of activation of the clusters. The yield of activation has been quantitatively calculated in a large animal dog model to be 24%. Furthermore, the reduction of the number of ACT® bubbles present as a function of time in each category component is estimated or retrieved from a database. The reduction of ACT® bubbles against time can be estimated by measuring the lifetime of the ACT® bubbles in different tissue types.

An example database giving component specific information is shown in Table 2, where only two frequencies are shown, for simplicity.

TABLE 2

| 1 | Tissue | Skin | Muscle | Fat | Parenchyma | Pancreas |
|---|---|---|---|---|---|---|
| 2 | Attenuation 0.5 MHz [dB/cm] | 0.91 | 0.31 | 0.35 | 0.29 | 0.42 |
| 3 | Attenuation 2 MHz [dB/cm] | 3.65 | 1.23 | 1.4 | 1.16 | 1.66 |
| 4 | Perfusion [mL/min/100 g] | 10 | 30 | 3 | 130 | 60 |
| 5 | Organ blood volume [%] | 5 | 5 | 5 | 15 | 10 |
| 6 | ACT ® bubble lifetime [min] | 5 | 5 | 5 | 5 | 5 |
| 7 | ACT ® bubble half-time [min] | 1.2 | 1.2 | 1.2 | 1.2 | 1.2 |
| 8 | ACT ® bubble activation yield [%] | 25 | 25 | 25 | 25 | 25 |

Wherein the MP is attenuation, contrast mode imaging ultrasound is suitable for use for attenuation estimation of the free-flowing contrast agent and fundamental B-mode imaging is suitable for use for estimation of attenuation due to the ACT® bubbles. This is due to the below reasons.

Contrast imaging modes will be more specific to backscatter signals generated from the free-flowing microbubble component, such as the commercially available microbubble contrast agents. These imaging modes exploit the nonlinear behaviors of the bubbles and extract out a nonlinear oscillation signature to form an image more dominated by the microbubble component and selectively suppressing backscatter signal from the tissue component. There is strong coupling of these microbubbles to diagnostic imaging pulses as the frequency of these pulses, around 2 to 10 MHz, is close the mechanical resonance of the bubble systems. Thus, bubble oscillations are significantly increased compared to insonation with off-resonance pulses. In contrast, ACT® bubbles have a resonance frequency of around 300 kHz. This resonance frequency is significantly lower than the diagnostic imaging frequency range. At diagnostic imaging frequencies the ACT® bubbles are being insonated above resonance and in this regime the scattering efficiency of the bubbles is much higher than the contrast agent scattering efficiency, wherein scattering efficiency is defined as a ratio of scatter to absorption cross section. Due to the increased size of the ACT® bubbles, they also produce significantly more backscatter (increased scattering cross section compared to free-flowing agents), such that they are easily visualized in fundamental B-mode. In this imaging mode a tissue contrast enhancement during fundamental B-mode imaging is dominated by the ACT® bubble component compared to the contrast agent. Thus, contrast mode imaging ultrasound is preferably used for attenuation estimation of the free-flowing contrast agent and fundamental B-mode imaging is preferably used for estimation of attenuation due to the ACT® bubbles.

Alternatively, further ACT®-specific imaging modes may be suitable for use in estimation of attenuation due to the ACT® bubbles.

Attenuation values over a frequency range for the activated ACT® clusters and the microbubble component of the clusters are retrieved. An example of such a database is given in Table 3, where only two frequencies are shown, for simplicity. The attenuation values are proportional to the concentration.

TABLE 3

| | Attenuation 0.5 MHz [dB/cm/(µL/mL)] | Attenuation 2 MHz [dB/cm/(µL/mL)] |
|---|---|---|
| Microbubble component | 0.16 | 2.78 |
| ACT ® bubbles (Activated cluster) | 20.0 | 1.50 |

The peak additional attenuation of the ultrasound pulses that arises from the injection of the ACT® clusters is calculated from the data provided in the database. For example, the peak attenuation from free-flowing ACT® microbubble clusters can be approximated by using a formula to calculate the concentration of the free-flowing bubbles for each tissue type. Using the patient's body weight, M, the ACT® injection dose per body weight, D, cardiac output, Q, organ blood volume fraction, $R_B$, injection duration, T, proportion of free-flowing bubbles in the injected formulation, r, and activation efficiency, η, the peak dose can be calculated as $$c_{FF}^{Peak}=(r+(1-\eta)(1-r))DMR_B/(\tau Q) \quad \text{Equation 9}$$

Similarly, the peak concentration of the ACT® bubbles may be calculated for each tissue type by using the following formula, where V is the total blood volume $$c_{ACT}^{Peak}=(1-r)\eta qDM/Q \quad \text{Equation 10}$$

Using the additional information, and assigning the values to the different segments of tissue types identified, the expected maximum attenuation for a given dose can be calculated as shown in Table 4, where a dose of 40 µL/kg has been used to calculate the attenuation from the microbubble and ACT® bubble components, based on the given equations and tables above.

TABLE 4

| | | Skin | Muscle | Fat | Parenchyma | Pancreas |
|---|---|---|---|---|---|---|
| Nominal derating [dB/cm] | 0.5 MHz | | | 0.15 | | |
| Tissue attenuation [dB/cm] | | 0.91 | 0.31 | 0.35 | 0.29 | 0.42 |
| Peak FF attenuation [dB/cm] | | 0.008 | 0.008 | 0.008 | 0.025 | 0.017 |
| Peak ACT ® attenuation [dB/cm] | | 0.030 | 0.089 | 0.009 | 0.386 | 0.178 |
| Layer attenuation, α [dB/cm] | | 0.95 | 0.41 | 0.37 | 0.71 | 0.61 |
| Nominal derating [dB/cm] | 2.0 MHz | | | 0.6 | | |
| Tissue attenuation [dB/cm] | | 3.65 | 1.24 | 1.4 | 1.16 | 1.66 |
| Peak FF attenuation [dB/cm] | | 0.152 | 0.152 | 0.152 | 0.455 | 0.303 |
| Peak ACT ® attenuation [dB/cm] | | 0.002 | 0.007 | 0.001 | 0.029 | 0.013 |
| Layer attenuation, α [dB/cm] | | 3.80 | 1.40 | 1.55 | 1.64 | 1.98 |
| Layer thickness [cm] | | 0.1 | 2.0 | 2.0 | 3.0 | 2.0 |

Once each category-specific MP value is adjusted to account for up to the respective category specific additional three elements of the ACT® therapy process correction, and attributed to each respective component, the method can then advance to step 214, wherein the (C) MP map is generated.

The presence of microbubbles and ACT® bubbles may affect sound speed and phase change. In a similar manner as to adding additional attenuation to each of the components of the segmented region of interest, the components in a MP map, for example a sound speed map or a phase change map, can be adjusted by the presence of microbubbles and ACT® bubbles also and via a similar manner as additional attenuation.

It is of particular importance to accurately control the ultrasound dose targeted to, and intended for oscillating, the ACT® bubbles since the bubbles will not oscillate enough if the ultrasound dose too far below the effective dose range. Lack of bubble oscillation and the desired ACT® therapeutic effect will not be achieved. However, an ultrasound dose too high above the effective dose range and the ACT® bubbles will oscillate too strongly, potentially leading to unwanted bioeffects. These unwanted bioeffects may include damage to the blood vessels and destruction of capillary walls. This may lead to a blocking of blood flow and result in less chemotherapy being delivered to tissue site than chemotherapy delivery without ACT® therapy. Thus, there is a window of ultrasound energy that is acceptable to drive drug delivery and achieve the desired ACT® therapy effects. Using the method of the invention herein described, this window of ultrasound energy (ultrasound dose) can be more easily and reliably controlled despite a subject's anatomy and composition and the presence of additional constituents for imaging and/or ACT® therapy.

Once the (C) MP is generated the method 200 is finished and the method according to 100 can advance to step 104, wherein computation of the attenuation values over the PP to calculate the PCF includes additional contrast agent correction for bubbles, for example the attenuation correction factor includes additional contrast agent attenuation and/or ACT® bubble attenuation.

Figure 5:
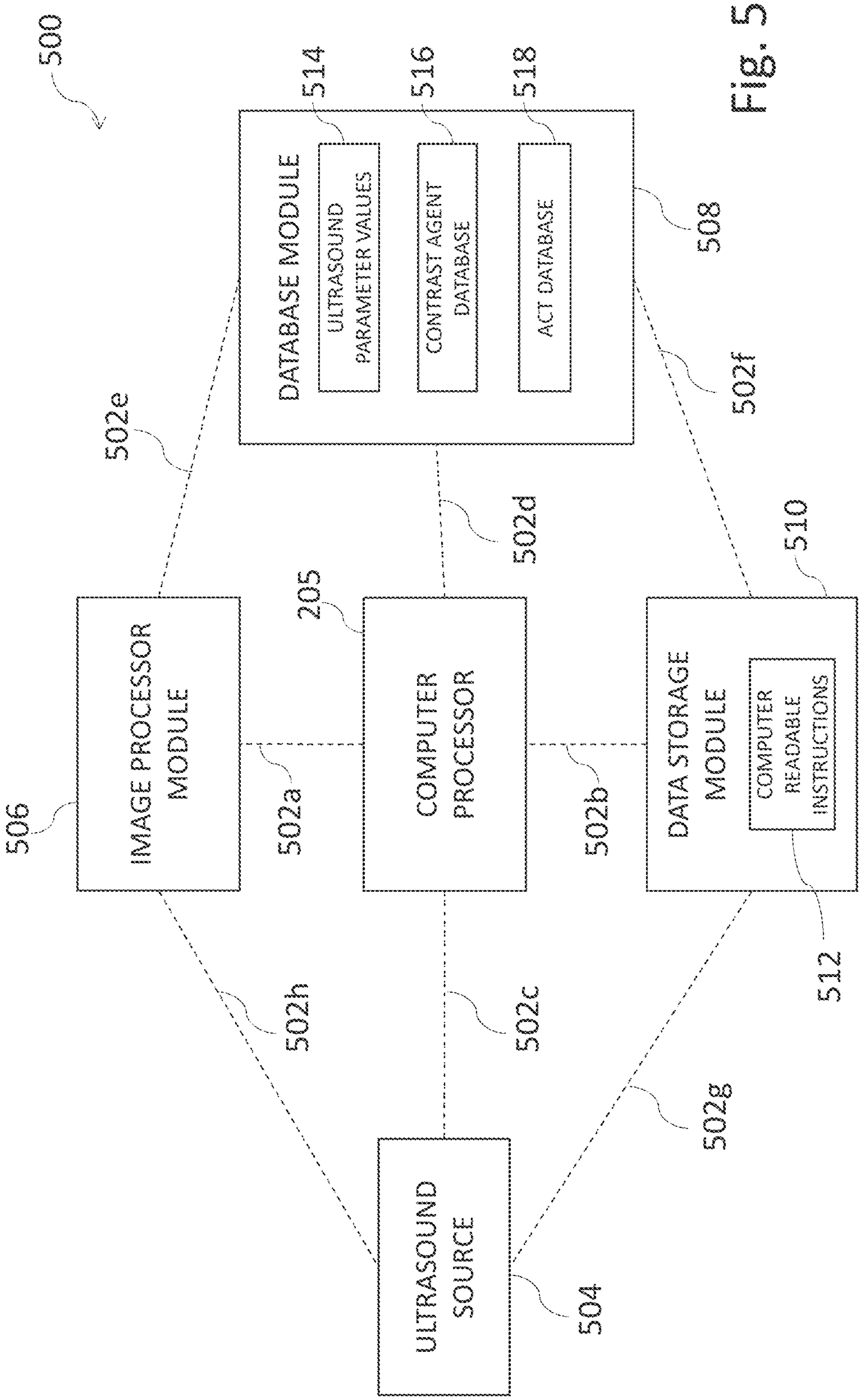
FIG. 5 is a system for calculating a point estimate of an ultrasound dose.

FIG. 5 is a schematic diagram of a system 500 both for generating a (C) MP map of a region of interest of a subject (method 200) and for calculating a point estimate of an ultrasound dose (method 100). System 500 has a computer processor 205, an ultrasound source 504, an image processor 506, a database module 508 and a data storage module 510. As demonstrated by the dashed lines 502*a-h*, each module of the system 500 is in data communication with each other module, either directly or via one of the other modules. The data storage module 510 contains computer readable instructions 502 that, when executed on the computer processor 205 perform the subsequent described tasks. From hereon the computer readable instructions when executed on the computer processor is referred to as the 'program' for simplicity.

First, the program instructs the image processor module 506 to process an image of the region of interest of a subject to segment the region of interest into its different components and categorize said components. The image processor 506 may segment and categorize the different components of the region of interest by identifying boundaries between different patterns of the image and analyzing the pattern within the boundaries compared to patterns of known tissue type to find a closest match. Over time, each processed image, and the associated attenuation map data can be used as historical data in the system 500 to accumulate more accurate segmentation and categorization capability of the image processor in the form of machine learning.

The program then instructs access to the MP value database 508, retrieves MP values for each of the identified categories and attributes the appropriate value to respective identified components. An example of a database comprising ultrasound parameter (MP) values for each of the identified categories (e.g. tissue types) is shown in Table 1. In this example table, values of attenuation in skin, muscle, fat, parenchyma, and pancreas and provided at a first frequency of 0.5 MHz and a second frequency 2 MHz. Preferably, MP value databases comprises ultrasound parameter values across a frequency range. Such data is publicly available in the art.

Preferably, the database module 508 further comprises a contrast agent microbubbles (or other ultrasound coupling bubble element) database 516 containing values for additional correction, for example attenuation, per unit concentration of different contrast agents. The database 516 may further contain retrievable values for:

blood volume for different subject weights;

cardiac output estimates for different subject weights;

typical values of blood volume for each component category;

typical arrival times after intravenous administration of different contrast agents for each component category; and concentration time curves for free-flowing contrast agent administered intravenously for each component category.

The program can retrieve the required values from the additional database 516 to estimate the additional correction, for example additional attenuation, from the presence of contrast agent in each category. Then, the additional correction can be added to each respective component MP value, for example attenuation value, prior to the program performing the step of computing the PCF over the PP.

As mentioned above, the peak additional attenuation of the ultrasound pulses that arise from the contrast agent microbubbles may be calculated from the data provided in the database. The peak attenuation from free-flowing contrast agent microbubbles can be approximated by using Equation 8 to calculate the concentration for the free-flowing bubbles for each tissue type.

In the presence of ACT® therapy, the database module 508 may comprise a database 518 containing values for estimating the additional correction resulting from three elements of the ACT® therapy process.

The database 518 may further contain retrievable values for:

total blood volume of subjects of different weight;

cardiac output of subjects of different weight;

a perfusion rate for each component category (Table 2, row 4);

a yield of activation of the ACT® microbubble clusters (Table 2, row 8);

a reduction of the number of ACT® bubbles present as a function of time in each category component (Table 2, row 7); and a lifetime of the ACT® bubbles in different tissue types (Table 2, row 6).

Alternatively to retrieving from a database, it is possible to determine the total volume of blood and the cardiac output of the patient via patient examination or by utilizing approximate values. For example, the blood volume and cardiac output can be estimated from the patient's body weight.

The program can calculate the peak additional attenuation of the ultrasound pulses that arises from the injection of the ACT® cluster from the data provided in the database. For example, the peak attenuation from free-flowing ACT® microbubbles clusters can be approximated by using Equation 9 to calculate the concentration of the free-flowing bubbles for each tissue type. The peak attenuation from activated ACT® bubbles can be approximated using Equation 10.

The program can retrieve the required values from the additional database 518 to estimate the additional correction from the presence of ACT® therapy in each category. Then the estimated additional correction is added to each respective component MP value prior to the program performing the step of computing the PCF over the PP.

A C (MP) map dependent on the geometry and tissue type, presence of contrast agent and/or presence of ACT® bubbles is thus generated and stored in the data storage module 510.

Values in the database module 516 may also be retrieved and used to estimate a correction due to the presence of microbubbles of the media properties: sound speed, shear wave velocity, acoustic impedance, coefficients of non-linear compressibility, and coefficients of dispersion, or derived properties, depending on the desired MP map. Further values in the database module 518 may also be retrieved and used to estimate additional correction due to the presence of ACT® bubbles to the above media properties. Thus, the respective sound speed map, shear wave velocity map, acoustic impedance map, coefficients of non-linear compressibility map, and coefficients of dispersion map (and any derived properties map) is dependent on the geometry and tissue type, presence of contrast agent and/or presence of ACT® bubbles may be generated and stored in the data storage module 510.

The database 508 and the data storage module 510 may be contained on the same or separate hardware devices. Alternatively, the database 508 and/or data storage module 510 are contained on a cloud-based platform.

Once the MP (for example attenuation) map has been generated, the program then delineates a PP, from the ultrasound source 504 to a target treatment area. The location of the ultrasound source 504 and the target treatment area is identified by the program or manually input by a user. The program then compiles the MP (for example attenuation) values for each component over the PP to generate the PCF, for example for attenuation.

The program uses the PCF (for example attenuation) to calculate the associated MI resulting from the specific PP to indicate the ultrasound dose insonated at the target area. Wherein the program generates a CMP map, several media properties are used to calculate one or several PCFs to calculate the associated MI and ultrasound dose.

The calculated path-specific MI/ultrasound dose is transmitted to the ultrasound source 504 (i.e. an ultrasound scanner). The ultrasound source may be adjusted in view of the calculated MI/ultrasound dose and the desired US dose for the target area.

In some examples of the invention, the system 500 is configured to perform a process of calculating the unique path-specific PCF, and thus, MI/ultrasound dose values, on a continuous basis. In this way as the ultrasound source 504 is moved with respect to the target area, and/or the ultrasound frequency is adjusted, the ultrasound dose can be tracked. If the ultrasound source remains in the region of interest, the system 500 does not need to generate a new (C) MP (e.g., attenuation) map. Thus, saving time and processing power.

As mentioned above, a large discrepancy (reduction) between actual tissue peak negative pressure from that given in the standard definition of MI renders this definition of MI unsuitable for some ultrasound applications. In particular, this is sub-optimal when a point estimate of peak rarefraction is needed for therapy applications. This is due to the simplified definition of MI which includes a simple power law dependency for attenuation and a single conservative value for tissue (for a safe upper limit). The recommended MI output for diagnostic imaging may accordingly not be the best for use in therapy. Hence, the method of the invention rather takes the propagation media constituents into account to estimate the ultrasound dose that should be delivered for therapy. Hence, the more accurate method according to the invention involves a step of categorising tissue types, present between the ultrasound transducer and the tissue volume to be treated, acknowledges the effect of bubbles (contrast agent, ACT® microbubble cluster and/or ACT®) in the respective tissue types and, in order to identify and define the ultrasound dose to be used in the therapy.

The PCF is needed to accommodate the particular environment that the ultrasound field traverses from the ultrasound source to the target area. As mentioned above the particular environment is dependent on a subject's anatomy and composition and the presence of additional constituents for imaging and/or ACT® therapy.

In the particular example wherein the MP is attenuation, there is a particular challenge for effective ACT® therapy using the current conservative, lower derating factor, with obese subjects. This is because the extra fat quantity in the ultrasound path results in a higher-than-average attenuation of the insonated ultrasound field and, thus, may result in an insufficient ultrasound dose delivered to the target treatment area. Since the method described herein can adjust for particular compositions, in terms of tissue type and geometry, the method herein is particular useful for ultrasound treatment in obese subjects.

Examples

A first example execution of the method of the invention described above is shown in FIGS. 6*a* to 6*c*.

Figure 6A:
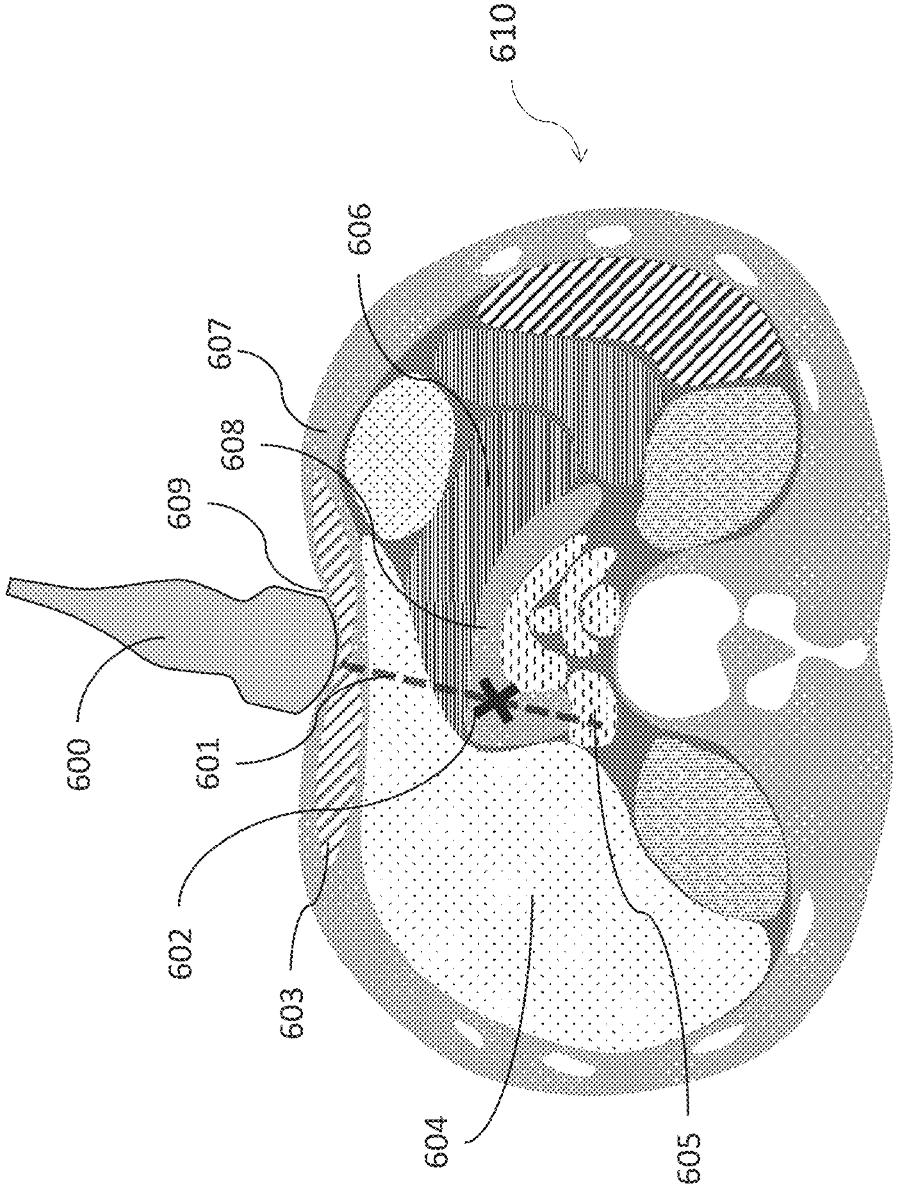
FIG. 6*a* is a diagram of the method being carried out according to a first example of the invention.

FIG. 6*a* shows a cross section of a human subject's abdomen 610. The cross section has muscle 603, liver 604, vessels 605, kidney 606, bone 607, spleen 608, intestine 609, stomach 610 and Pancreas 611. An ultrasound transducer 600 is put into contact with an external skin surface of the human subject's abdomen 610. The ultrasound transducer 600 transmits an ultrasound field along an acoustic path 601 towards a target depth indicated by a cross 602. As shown in the diagram, the acoustic path 601 passes through organs of several different type between the ultrasound transducer 600 and target 602 i.e., skin, muscle 603, fat, liver 604, intestine 609, and pancreas 311.

In the example of FIG. 6*a*, the acoustic path 601 is shown as a single linear path from a discrete point of the transducer 600 to the target 602. However, the acoustic path may be made up of a plurality of ultrasound rays having their respective path, as mentioned above.

Figure 6B:
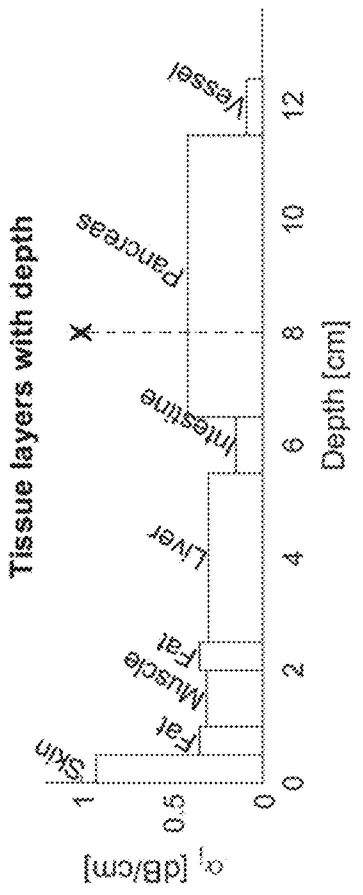
FIG. 6*b* is a graph of tissue layer against depth according to the method of the first example.

FIG. 6*b* shows a graph of attenuation coefficient against depth along the acoustic path 601 of FIG. 6*a*, the attenuation coefficient dependent on the type of tissue being traversed at that depth. In the example of FIG. 6*b*, the attenuation coefficient at a depth between 0 cm and approximated 0.5 cm is 0.4 i.e., that of skin. The attenuation coefficient at a depth between approximately 0.5 cm and 1.0 cm and between 2.0 cm and 2.5 cm is 0.3 i.e., that of fat. The attenuation coefficient at a depth between approximately 1.0 cm and 2.0 cm is 0.5 i.e., that of muscle. The attenuation coefficient at a depth between approximately 2.5 cm and 5.5 cm is that of the liver around 0.35. At a depth of 5.5 to 6.5 the acoustic path crosses the intestine, the intestine tissue having an attenuation coefficient of around 1.5. The final tissue type traversed by the ultrasound field prior to reaching the target is pancreas 608 organ tissue having an attenuation coefficient of around 0.25 dB/cm.

Figure 6C:
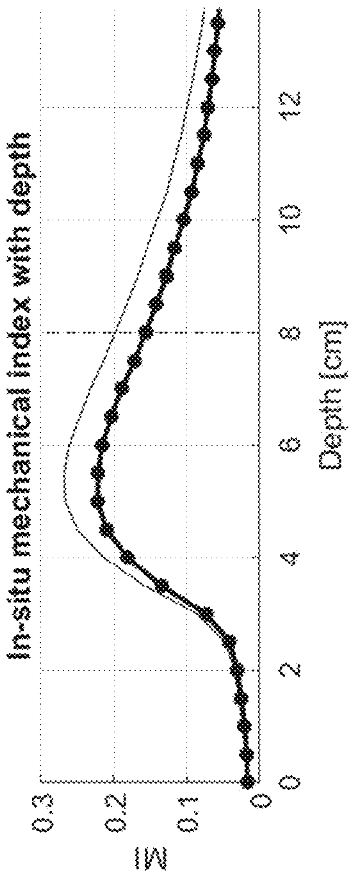
FIG. 6*c* is a graph of MI against depth according to the first example.

FIG. 6*c* shows a graph of a resulting mechanical index (Equation 5) against depth along the acoustic path 602. The solid line represent a mechanical index adjusted for standard derating of 0.3 dB/cm/MHz and the thick solid line with dots represents the mechanical index adjusted for medium specific attenuation, in the example of FIG. 6*c* the media of 6*b*. Thus, the thick solid line with dots represents pressure according to Equation 5 when $\alpha \rightarrow \alpha_{CF}$. At the target, the mechanical index is approximately 0.15.

A second example execution of the method of the invention described above is shown in FIGS. 7*a* to 7*c*.

Figure 7A:
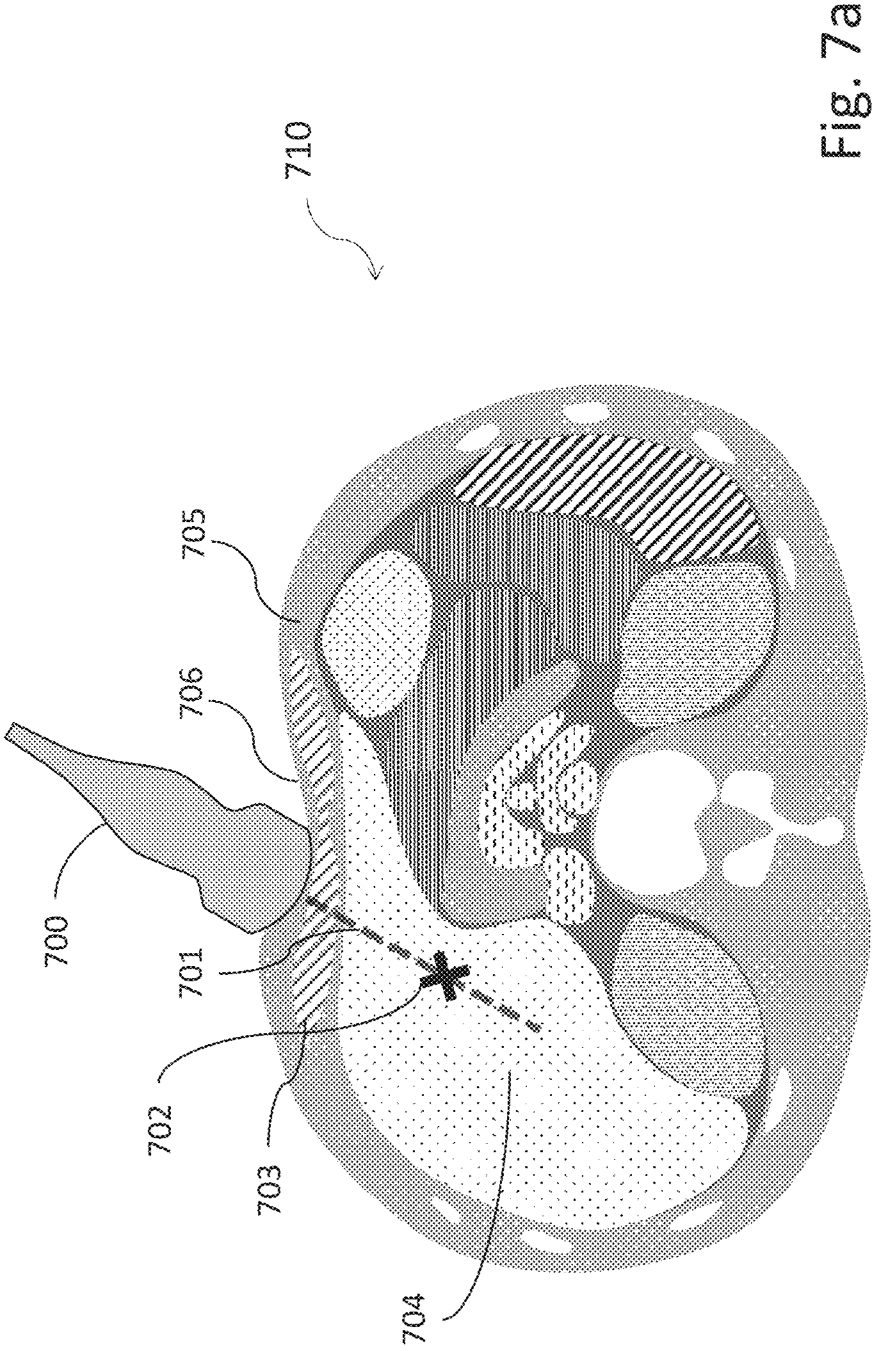
FIG. 7*a* is a diagram of the method being carried out according to a second example of the invention.

FIG. 7*a* shows a cross section of a human subject's abdomen 710. The cross section shows tissue from muscle 703, liver 704, fat 705 and skin 706. An ultrasound transducer 700 is put into contact with an external skin surface of the human subject's abdomen 710. The ultrasound transducer 700 transmits an ultrasound field along an acoustic path 701 towards a target depth indicated by a cross 702. As shown in the diagram, the acoustic path 701 passes through organs of several different type between the ultrasound transducer 700 and target 702 i.e., skin 706, fat 705, muscle 703, fat 705 and liver, all comprising microbubbles and ACT® bubbles.

Similarly to example 6a, in the example of FIG. 7*a*, the acoustic path 701 is shown as a single linear path from a discrete point of the transducer 700 to the target 702. However, the acoustic path may be made up of a plurality of ultrasound rays having their respective path, as mentioned above.

Figure 7B:
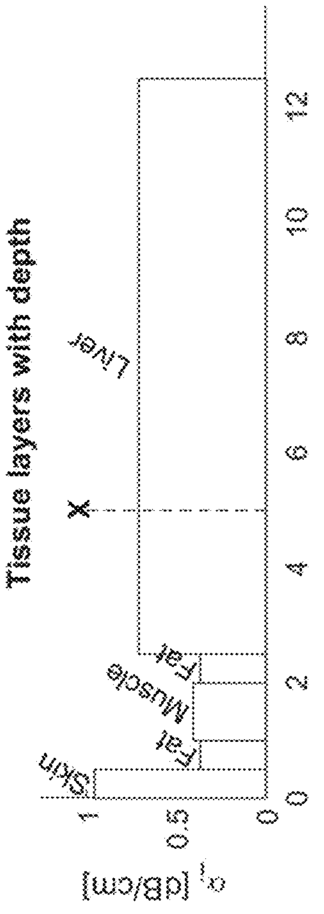
FIG. 7*b* is a graph of tissue layer against depth according to the second example.

FIG. 7*b* shows a graph of attenuation coefficient against depth along the acoustic path 701 of FIG. 7*a*, the attenuation coefficient dependent on the type of tissue being traversed at that depth. In the example of FIG. 7*b*, the attenuation coefficient at a depth between 0 cm and approximately 0.5 cm is 0.96 dB/cm i.e., that of skin having a presence of microbubbles and ACT® bubbles. The attenuation coefficient at a depth between approximately 0.5 cm and 1.0 cm and between 2.0 cm and 2.5 cm is 0.37 dB/cm i.e., that of fat having a presence of microbubbles and ACT® bubbles. The attenuation coefficient at a depth between approximately 1.0 cm and 2.0 cm is 0.41 dB/cm i.e., that of muscle having a presence of microbubbles and ACT® bubbles. The attenuation coefficient at a depth between approximately 2.5 cm and the target 502 at a depth of around 5.0 cm is 0.71 dB and is the attenuation coefficient of liver tissue having a presence of microbubbles and ACT® bubbles.

Figure 7C:
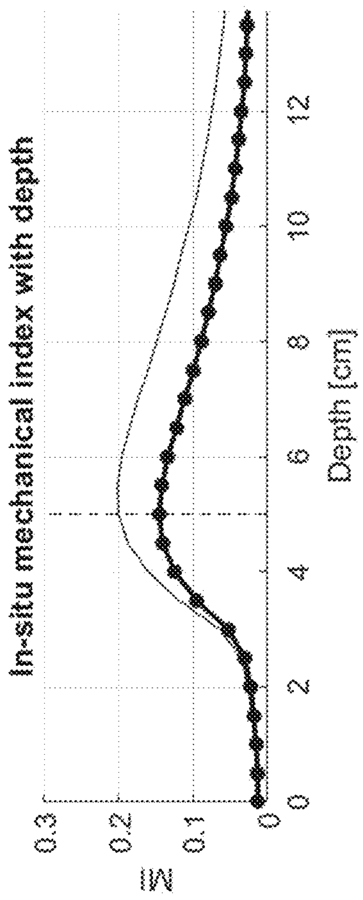
FIG. 7*c* is a resultant graph of MI against depth according to the second example.

FIG. 7*c* shows a graph of a resulting mechanical index against depth along the acoustic path 702. The thick solid line with dots represents a resultant mechanical index adjusting for medium specific attenuation whereas the solid line represents a resultant mechanical index adjusted for standard attenuation (0.3 dB/cm/MHz), in the example of FIG. 7*c* the media of 7*b*. At the target depth, the mechanical index is approximately 0.15.

The examples of the method as demonstrated by example 1 according to FIGS. 6*a* to 6*c* and example 2 according to FIGS. 7*a* to 7*c* demonstrate the dependence of pressure with tissue type and with and without the presence of bubbles in the tissue.

As an example, a target area is a metastatic lesion that is located in the liver of a patient. The patient receives a treatment consisting of a chemotherapeutic drug that is injected as an infusion, and the treatment is enhanced by injecting a dose of ACT® clusters and performing activation and enhancement ultrasound at the target lesion. The treatment ultrasound is provided from an ultrasound scanner with a connected ultrasound probe that is placed in contact with the skin on the patient's abdomen, such as is shown in FIGS. 6*a* and 7*a*. Prior to treatment, the preferred probe placement is determined based on ultrasound imaging of the patient. When the preferred placement is determined, tissue types present between the probe and the target lesion are identified. This process can be done by a segmentation algorithm using a trained artificial intelligence that can access the ultrasound scanner data. One or more lines of sight are delineated from the probe face to the target lesion, and the thickness of each segment along this line is calculated. Typically for this situation, the ultrasound field emitted by the probe transverses layers of skin, fat, muscle, and liver parenchyma before reaching the target lesion. The medium property map is created by the ultrasound scanner by retrieving from a database, for each tissue type, the values for tissue perfusion, ACT® bubble lifetime, ACT® bubble half-time, ACT® bubble activation yield, and ultrasound attenuation over a frequency range. An example of such a database is given in the Table 2.

Furthermore, attenuation values over a frequency range for the activated ACT® clusters and the microbubble component of the clusters are retrieved. An example of such a database is given in the Table 3, where only two frequencies are shown, for simplicity. The attenuation values are proportional to the concentration.

It is possible to determine the total volume of blood and the cardiac output of the patient via patient examination or by utilizing approximate values. For example, the blood volume and cardiac output can be estimated from the patient's body weight. In this example, the patient's body weight is 70 kg, and is provided as input to the ultrasound scanner. This number is used by the algorithm to calculate a blood volume of 4.6 L, and a cardiac output of 5 L/min. The ACT® clusters are injected over a period of 30 seconds, so for the first pass through the circulatory system, the dose is mixed in a limited blood pool.

The peak additional attenuation of the ultrasound pulses that arises from the injection of the ACT® clusters is calculated from the data provided in the database. For example, the peak attenuation from free-flowing microbubbles can be approximated by using a Equation 9.

Similarly, the peak concentration of the ACT® bubbles may be calculated for each tissue type by using the following Equation 10.

Using the additional information, and assigning the values to the different segments of tissue types identified, the algorithm can calculate the expected maximum attenuation for a given dose as shown in Table 4, where a dose of 40 uL/kg has been used to calculate the attenuation from the microbubble and ACT® bubble components.

In the example described with the values given and using discrete integration along the specified line of sight give a total attenuation of 5.0 and 15.2 dB at 0.5 and 2 MHZ, respectively, compared to the standard derating of 1.4 and 5.5 dB obtained by using the standard derating.

Figure 8:
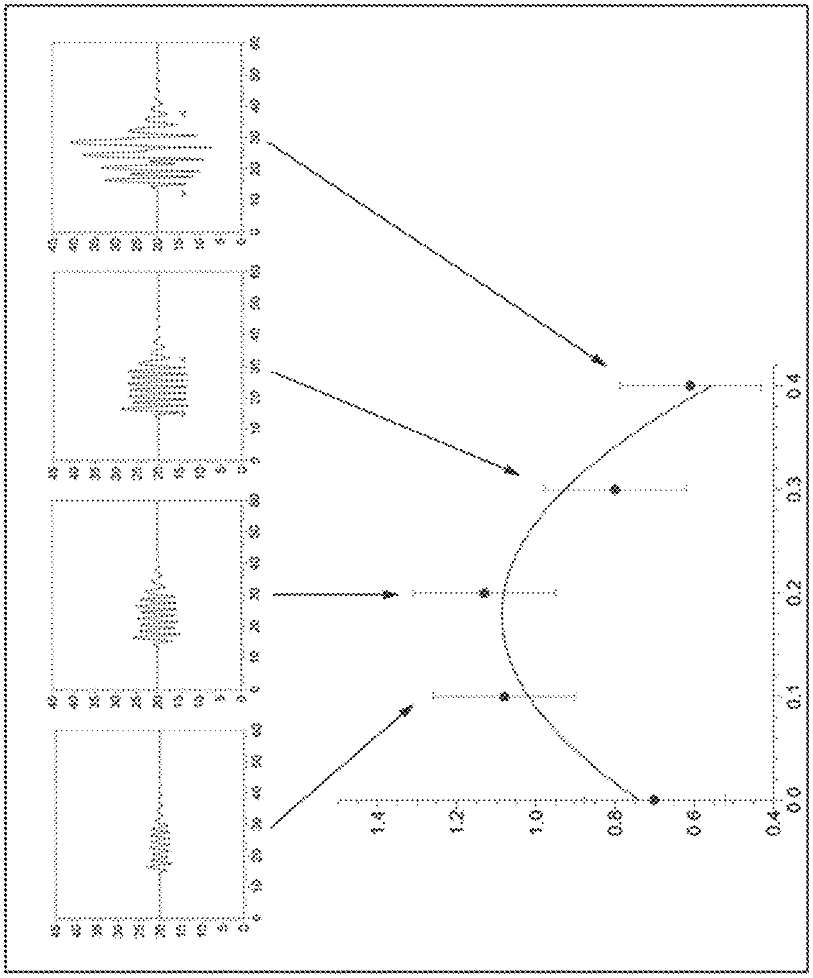
FIG. 8 provides results for tumour specific uptake of a fluorescent dye upon ACT® treatment with an Enhancement step insonation field.

As mentioned above, it is of particular importance to accurately control the ultrasound dose targeted to, and intended for oscillating, the ACT® bubbles since the bubbles will not oscillate enough if the ultrasound dose too far below the effective dose range. This is demonstrated in FIG. 8 which provides results for tumour specific uptake of a fluorescent dye (Evans Blue) upon ACT® treatment with an Enhancement step insonation field at 500 kHz, with mechanical indices (MIs) at 0, 0.1, 0.2, 0.3 and 0.4 (lower panel). Y-axis shows tumour specific uptake in mg Evans Blue/mg tumour tissue. X-axis shows mechanical index. The four upper panels show results from modelling of activated bubble response to the incident US field at the different MIs investigated. Y-axis shows the radius of the activated bubble in μm. X-axis shows time in μ-seconds.

To investigate the effect of MI variance of the US Enhancement field, tumour specific uptake of Evans Blue (EB, fluorescent dye) has been investigated in a subcutaneous prostate cancer model (PC3) in mice. Five groups with Enhancement insonation MIs of 0, 0.1, 0.2, 0.3 and 0.4 were investigated (N=3 animals per group). Immediately after i.v. injection of EB, a single dose of cluster composition (2 mL/kg, (i.v.)) was given followed by 45 sec Activation US (2.25 MHz, MI 0.4) and 5 min Enhancement US (0.5 MHz, variable MI), focused to the tumour volume. 30 min after treatment, the tumours were excised and the amount of EB was measured by spectrophotometry at 620 nm.

Tissue uptake of Evans blue and bubble oscillations as a function of MI. Results are visualized in FIG. 8. As can be noted, the tissue uptake increases from no US (MI=0) to MI=0.1 and further with MI=0.2, but then drops again with MI=0.3 and further with M=0.4. At an MI of 0.2 an almost 60% increase in tumour specific uptake is observed, compared to MI=0 (no ultrasound). At the same time, from the embedded bubble oscillation panels, maximum radial oscillation increases from approx. 3 μm at MI=0.1, to approx. 6 μm at MI=0.2, to approx. 10 μm at MI=0.3 and more than to 20 μm at MI=0.4. Importantly, then onset of a reduction in tissue uptake (from MI=0.2 to MI=0.3) is concurrent with the onset of significant non-linear behaviour, where inertial cavitation starts to occur.

The invention shall not be limited to the shown embodiments and examples. While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is to be understood that various alternatives to the embodiments described herein can be employed in practicing the disclosure.

It is to be understood that every embodiment of the disclosure can optionally be combined with any one or more of the other embodiments described herein.

It is to be understood that each component, compound, particle, or parameter disclosed herein is to be interpreted as being disclosed for use alone or in combination with one or more of each and every other component, compound, or parameter disclosed herein. It is further to be understood that each amount/value or range of amounts/values for each component, compound, or parameter disclosed herein is to be interpreted as also being disclosed in combination with each amount/value or range of amounts/values disclosed for any other component(s), compound(s), or parameter(s) disclosed herein, and that any combination of amounts/values or ranges of amounts/values for two or more component(s), compound(s), or parameter(s) disclosed herein are thus also disclosed in combination with each other for the purposes of this description. Any and all features described herein, and combinations of such features, are included within the scope of the present invention provided that the features are not mutually inconsistent.

It is to be understood that each lower limit of each range disclosed herein is to be interpreted as disclosed in combination with each upper limit of each range disclosed herein for the same component, compound, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, or parameter disclosed in the description or an example is to be interpreted as a disclosure of either a lower or an upper limit of a range and thus can be combined with any other lower or upper limit or a range or specific amount/value for the same component, compound, or parameter disclosed elsewhere in the application to form a range for that component, compound, or parameter.

Having described preferred examples of the invention it will be apparent to those skilled in the art that other embodiments incorporating the invention may be used. These and other examples of the invention illustrated above are intended by way of example only and the actual scope of the invention is to be determined from the appended claims.

The invention claimed is:

1. A system for providing a point estimate of an ultrasound dose at a region of interest in a subject comprising:

an ultrasound source;

an image processor module for processing images to identify different components of the region of interest;

a computer processor;

a database module comprising medium property values associated with a plurality of categories for components within the region of interest;

a data storage module comprising computer readable instruction that when executed on the processor perform the tasks of:

retrieving an image of the region of interest, wherein the region of interest comprises a target treatment area and a surrounding region of the target treatment area;

processing the image to identify different components of the region of interest;

segmenting and categorizing the different components into predetermined media categories;

retrieving a medium property value associated with each media category, comprising;

estimating a category-specific ultrasound coupling bubble element correction to the medium property value resulting from the presence of at least one ultrasound coupling bubble element in at least one component; and adjusting the medium property value of the at least one component to account for the respective category-specific ultrasound coupling bubble element correction; and attributing said medium property value to each respective component of the segmented region of interest; and delineating an ultrasound propagation path from the ultrasound source to the target treatment region;

compiling the medium property values for each component over the propagation path to calculate an ultrasound propagation correction factor unique to the ultrasound propagation path through the region of interest;

calculating the point estimate of the ultrasound dose at the region of interest based on the unique propagation correction factor; and adjusting the ultrasound source according to the calculated point estimate of the ultrasound dose if outside of a predetermined ultrasound dose range.

2. The system of claim 1, wherein the image processor is configured to segment and categorize the different components of the region of interest by:

identifying boundaries between different patterns of the image;

analyzing the pattern within the boundaries; and comparing each of the patterns to image patterns of known tissue type to find a match.

3. The system of claim 2, wherein the system is a machine learning system and wherein each processed image, along with associated image data, is accumulated as training data to provide more accurate segmentation and categorization by the image processor over time.

4. The system of claim 1, further comprising an ultrasound probe providing the ultrasound source, the system further configured to:

track the ultrasound probe position;

re-evaluate one or more propagation correction factors with movement of the ultrasound probe position; and store a one or more propagation correction factors per ultrasound probe position to reduce a computational load.

5. The system of claim 1, further configured to:

track an in-plane and out-of-plane rhythmic movement of the medium of the region of interest;

re-evaluate one or more propagation correction factors for each in-plane and out-of-plane position of the moving medium; and store the one or more propagation correction factors for each in-plane and out-of-plane position of the moving medium.

6. The system of claim 5, wherein the system is configured to track the in-plane and out-of-plane rhythmic movement of the medium through speckle-tracking or machine learning algorithms.

7. The system of claim 1, wherein the media categories comprise at least one of:

different tissue types;

different tissue types afflicted by one or more particular diseases;

a fluid; and a gas.

8. The system of claim 7, wherein the different tissue types comprise one or more of:

soft tissue comprising fat, muscle, parenchyma, tendons and ligaments; and hard tissue comprising bone.

9. The system of claim 8, wherein calculating the correction resulting from the presence of contrast agent in each category is based on contrast mode imaging ultrasound.

10. The system of claim 7, wherein the at least one ultrasound coupling bubble element comprises ACT bubble technology ultrasound coupling bubble elements and wherein calculating an additional ACT bubble correction comprises:

estimating additional correction resulting from ACT microbubble clusters in the presence of the high frequency activation ultrasound;

estimating additional correction resulting from generated ACT bubbles in the presence of the high frequency activation ultrasound; and estimating additional correction resulting from ACT bubbles in the presence of low frequency enhancement ultrasound.

11. The system of claim 10, wherein calculating additional ACT bubble correction further comprises:

estimating a number of ACT bubbles in the categories associated with each component by:

retrieving or estimating one or more ACT bubble parameters, wherein the ACT bubble parameters comprise:

a blood volume of the subject;

a cardiac output of the subject;

a perfusion of each category of components; and a time concentration curve; and calculating the number of ACT bubbles delivered to each of the components by multiplying a fraction of the cardiac output that accounts for the perfusion of each category of components by a yield of activation of ACT bubble clusters.

12. The system of claim 11, wherein the estimation of the number of ACT bubbles in the categories associated with each segment comprises a time dependency by:

retrieving a value for a lifetime of an ACT bubble in each category to model a reduction of the number of ACT bubbles in each category over time.

13. The system of claim 1, wherein the retrieving the image of the region of interest comprises at least one of:

retrieving a pre-scanned scan of the region of interest;

taking a pre-scan scan of the region of interest; and using a real-time diagnostic imaging system image.

14. The system of claim 13, wherein the scan comprises one or more of:

a computer tomography image; and a magnetic resonance image.

15. The system of claim 14, wherein calculating the additional correction resulting from the presence of ACT bubbles in each category is based on fundamental B-mode imaging ultrasound.

16. The system of claim 13, wherein the at least one ultrasound coupling bubble element comprises one or more of:

contrast agent microbubbles;

cavitation seeds;

large microbubbles;

acoustic cluster therapy (ACT) bubble technology ultrasound coupling bubble elements, wherein the ACT bubble technology ultrasound coupling bubble elements comprise:

ACT microbubble clusters; and activated ACT bubbles.

17. The system of claim 16, wherein the at least one ultrasound coupling bubble element comprises contrast agent microbubbles and wherein estimating a contrast agent microbubble correction comprises:

retrieving or estimating contrast agent microbubble parameters, wherein the contrast agent microbubble parameters comprise:

a value for the dose of contrast agent microbubbles administered;

contrast agent attenuation per unit concentration;

a blood volume of the subject;

a cardiac output of the subject;

a value of blood volume associated with each category;

arrival times after intravenous administration of the contrast agent for each category; and a time concentration curve; and using the contrast agent parameters to calculate the contrast agent correction for each category.

18. The system of claim 1, further comprising using the unique propagation correction factor to calculate at least one of a resulting pressure, a resulting mechanical index, a resulting intensity, a resulting power and a resulting thermal index, which are indications of delivered ultrasound dose.

19. The system of claim 1, wherein the medium property comprises at least one of attenuation, sound speed, shear wave velocity, acoustic impedance, coefficients of nonlinear compressibility, and coefficients of dispersion.

20. The system of claim 19, wherein the medium property further comprises one or more derived properties that can be derived from any one, or any combination, of the medium properties listed.

* * * * *